(12) United States Patent
Petro et al.

(10) Patent No.: US 6,730,228 B2
(45) Date of Patent: May 4, 2004

(54) METHODS AND APPARATUS FOR CHARACTERIZATION OF POLYMERS USING MULTI-DIMENSIONAL LIQUID CHROMATOGRAPHY WITH REGULAR SECOND-DIMENSION SAMPLING

(75) Inventors: Miroslav Petro, San Jose, CA (US); Son Hoai Nguyen, Santa Clara, CA (US); Eric D. Carlson, Cupertino, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 10/230,863

(22) Filed: Aug. 28, 2002

(65) Prior Publication Data

US 2003/0080062 A1 May 1, 2003

Related U.S. Application Data

(60) Provisional application No. 60/315,685, filed on Aug. 28, 2001.

(51) Int. Cl.[7] ............................................. B01D 15/08
(52) U.S. Cl. ...................... 210/656; 210/659; 210/143; 210/198.2
(58) Field of Search ................................ 210/635, 656, 210/659, 143, 198.2; 73/61.52; 436/161

(56) References Cited

U.S. PATENT DOCUMENTS

| | | | |
|---|---|---|---|
| 3,236,603 A | 2/1966 | Durrett et al. ................. 422/89 |
| 3,458,437 A | 7/1969 | Ouano | |
| 3,518,059 A | 6/1970 | Levy et al. .................. 436/158 |
| 3,522,172 A | 7/1970 | Pretorius et al. | |
| 3,649,200 A | 3/1972 | Moore | |
| 3,703,798 A | 11/1972 | Pretorius et al. ................ 95/82 |
| 3,773,470 A | 11/1973 | Rouzier ...................... 422/110 |
| 3,791,522 A | 2/1974 | Eisenbeiss ............... 210/198.2 |
| 3,926,589 A | 12/1975 | Klementi et al. ............... 95/86 |
| 4,036,063 A | 7/1977 | Roof et al. .............. 73/863.71 |

(List continued on next page.)

FOREIGN PATENT DOCUMENTS

| | | |
|---|---|---|
| DE | 2731652 | 1/1979 |
| DE | 19704477 A1 | 2/1997 |
| DE | 19641210 | 4/1998 |
| EP | 0 359 322 A2 | 3/1990 |

(List continued on next page.)

OTHER PUBLICATIONS

Stalling,"Application of Analytical Mehtods Research to Monitoring Organic Residues in Fish", 1976,Int.Conf.on Environmental Sensing and Assesment vol. 1.XP002225031,N.Y.

Kilz et al.,"Two Dimensional Chromatography for the Deformulation of Complex Copolymers",Amer. Chem. Soc., 1995,pp. 223–241.

Chen H.et al."High–Speed High–Performance Liquid Chromatography of Peptides and Proteins",J. of Chromatography A,NL, vol. 705–1.June 23, 1995, pp. 3–20.

(List continued on next page.)

Primary Examiner—Ernest G. Therkorn
(74) Attorney, Agent, or Firm—Summa & Allan, P.A.

(57) ABSTRACT

Methods and apparatus for characterizing a polymer sample and in preferred embodiments, libraries of polymer samples, in a comprehensive, directly-coupled multi-dimensional liquid chromatography system are disclosed. The first and second dimensions are preferably high-performance liquid chromatography dimensions, such as for example, a first dimension adapted for determining composition (e.g. adapted for mobile-phase gradient elution chromatography, including reverse phase chromatography, adsorption chromatography and the like), and a second dimension adapted for determining molecular weight or particle size (e.g., adapted for size exclusion chromatography, including gel permeation chromatography).

41 Claims, 10 Drawing Sheets

U.S. PATENT DOCUMENTS

| | | | |
|---|---|---|---|
| 4,159,897 A | 7/1979 | Doehlert | 44/282 |
| 4,280,923 A | 7/1981 | Small et al. | |
| 4,313,906 A | 2/1982 | Filipi et al. | 422/69 |
| 4,469,601 A | 9/1984 | Beaver et al. | 210/658 |
| 4,476,026 A | 10/1984 | Katz et al. | |
| 4,532,043 A | 7/1985 | Prud'homme et al. | |
| 4,674,323 A | 6/1987 | Rulf et al. | |
| 4,728,344 A | 3/1988 | Stacy | 95/25 |
| 4,798,081 A | 1/1989 | Hazlitt et al. | |
| 4,821,303 A | 4/1989 | Fawcett et al. | 378/80 |
| 4,930,898 A | 6/1990 | Miller-Ihli | 366/109 |
| 4,935,145 A | 6/1990 | Cortes et al. | 210/656 |
| 4,980,130 A | 12/1990 | Metzger et al. | 422/70 |
| 4,992,168 A | 2/1991 | Takayama et al. | 210/198.2 |
| 5,008,204 A | 4/1991 | Stehling | |
| 5,039,614 A | 8/1991 | Dekmezian et al. | 436/43 |
| 5,089,126 A | 2/1992 | Silebi et al. | |
| 5,106,756 A | 4/1992 | Zaromb | 436/161 |
| 5,116,764 A | 5/1992 | Annino et al. | 436/161 |
| 5,132,012 A | 7/1992 | Miura et al. | |
| 5,135,549 A | 8/1992 | Phillips et al. | 95/8 |
| 5,139,680 A | 8/1992 | Tarnopolsky | 210/656 |
| 5,185,429 A | 2/1993 | Cinquina et al. | 528/503 |
| 5,190,882 A | 3/1993 | Schultz et al. | |
| 5,196,039 A | 3/1993 | Phillips et al. | |
| 5,240,604 A | 8/1993 | Cortes et al. | |
| 5,277,871 A | 1/1994 | Fujii et al. | |
| 5,316,680 A | 5/1994 | Frechet et al. | 210/635 |
| 5,334,310 A | 8/1994 | Frechet et al. | |
| 5,352,612 A | 10/1994 | Huber et al. | |
| 5,376,277 A | 12/1994 | Cortes et al. | 210/659 |
| 5,398,539 A | 3/1995 | Gordon et al. | 73/23.35 |
| 5,474,744 A | 12/1995 | Lerch | 422/100 |
| 5,492,831 A | 2/1996 | Ranger | 436/50 |
| 5,508,204 A | 4/1996 | Norman | 436/161 |
| 5,531,959 A | 7/1996 | Johnson et al. | 422/70 |
| 5,585,236 A | 12/1996 | Bonn et al. | |
| 5,587,082 A | 12/1996 | Teraoka et al. | |
| 5,597,733 A | 1/1997 | Bell et al. | 436/54 |
| 5,603,899 A | 2/1997 | Franciskovich et al. | |
| 5,651,885 A | 7/1997 | Schick | |
| 5,667,676 A | 9/1997 | Alaska | |
| 5,670,054 A | 9/1997 | Kibbey et al. | |
| 5,711,786 A | 1/1998 | Hinshaw | |
| 5,738,783 A | 4/1998 | Shirota et al. | 210/198.2 |
| 5,746,982 A | 5/1998 | Saneii et al. | 422/134 |
| 5,766,481 A | 6/1998 | Zambias et al. | |
| 5,773,305 A | 6/1998 | Zabetakis et al. | 436/179 |
| 5,777,213 A | 7/1998 | Tskazaki et al. | |
| 5,795,469 A | 8/1998 | Quinn et al. | |
| 5,814,742 A | 9/1998 | Vissers et al. | 73/863.73 |
| 5,827,426 A | 10/1998 | Fujii et al. | |
| 5,833,861 A | 11/1998 | Afeyan et al. | |
| 5,866,004 A | 2/1999 | Houck et al. | 210/634 |
| 5,897,837 A | 4/1999 | Mizuno | 422/100 |
| 5,919,368 A | 7/1999 | Quinn et al. | |
| 5,938,931 A | 8/1999 | Ono et al. | |
| 5,938,932 A | 8/1999 | Connelly et al. | 210/659 |
| 5,948,360 A | 9/1999 | Rao et al. | 422/65 |
| 5,959,297 A | 9/1999 | Weinberg et al. | 250/288 |
| 5,968,361 A | 10/1999 | Goetzinger et al. | |
| 5,985,120 A | 11/1999 | Cholli et al. | |
| 5,985,356 A | 11/1999 | Schultz et al. | 427/8 |
| 6,017,767 A | 1/2000 | Chandler | 436/514 |
| 6,054,047 A | 4/2000 | Hindsgaul et al. | |
| 6,058,764 A | 5/2000 | Yamada et al. | |
| 6,063,138 A | 5/2000 | Hanna et al. | 23/295 R |
| 6,077,438 A | 6/2000 | Zambias et al. | |
| 6,080,318 A | 6/2000 | Gumm et al. | |
| 6,156,273 A | 12/2000 | Regnier et al. | 422/70 |
| 6,175,409 B1 | 1/2001 | Nielson et al. | |
| 6,197,198 B1 | 3/2001 | Messinger et al. | 210/656 |
| 6,210,571 B1 | 4/2001 | Zambias et al. | |
| 6,260,407 B1 | 7/2001 | Petro et al. | |
| 6,265,226 B1 | 7/2001 | Petro et al. | |
| 6,294,388 B1 | 9/2001 | Petro | |
| 6,296,771 B1 | 10/2001 | Miroslav | |
| 6,306,658 B1 | 10/2001 | Turner et al. | |
| 6,406,632 B1 | 6/2002 | Safir et al. | |
| 6,436,292 B1 | 8/2002 | Petro | |
| 6,475,391 B2 | 11/2002 | Safir et al. | |
| 6,491,816 B2 | 12/2002 | Petro | |

FOREIGN PATENT DOCUMENTS

| | | |
|---|---|---|
| EP | 0655624 | 5/1995 |
| EP | 1 089 074 A1 | 4/2001 |
| GB | 2290283 | 12/1995 |
| JP | 60115854 | 6/1985 |
| WO | WO 96/11878 | 4/1996 |
| WO | WO 97/01755 A2 | 1/1997 |
| WO | WO 97/16724 | 5/1997 |
| WO | WO 97/32208 | 9/1997 |
| WO | WO 98/13118 | 4/1998 |
| WO | WO 00/57170 | 9/2000 |

OTHER PUBLICATIONS

Berek et al."Columns Packings for High Performance Liquid Chromatography: Present State and Future Development",J.of Radioana.&Nuclear Chem.Art183, 1994, pp. 19–26.

Barth et al."Size Exclusion Chromatography and Related Seperation Techniques", Anal. Chem., 70(12),pp. 251–278.

Blom et al."Determining Affinity–Selected Ligands and Estimation Binding Affinities by Online Size Exclusion Chromatography/Liquid Chromatography–Mass Spectrometry", 1999,J.Comb.Chem.1.pp. 82–90.

Brocchini et al."A Combinatorial Approach for Polymer Design", 1997,J.Am. Chem. Soc 119, pp. 4553–455.

Dawkins et al."Rigid Polyacrylamide Gels for High–Performance Size–Exclusion Chromatography",J.Chromatography 371, 1986, pp. 283–391.

Gilson Advertisement for Multiple Probe with 889 Injection Module.

Glockner,G."Chromatographic Cross–Fractionation",May 1, 1988,Trac.Trends in Anal. Chem.,Anal. Chem.,Cambridge,GB.V 7, pp. 169–173.

Yau et al.,"Section 11.5 High Speed Process", 1979,SEC,pp. 378–379.

Zisenis et al.,"Changes of Macromolecular Chain Conformations Induced by Shear Flow", 1995,Amer.Chem.Soc., Chap.7,pp. 91–104.

Zeng,Lu."Developments of a Fully Automated Parallel HPLD/Mass Spectrometry System for the Analytical Characterization and Preparative Purification of Combinatorial Libraries", 1998,Anal. Chem.,vol. 70, pp. 4380–4388.

Scholten et al."Fluorescence Detection of Chloroanilines in Liquid Chromatography Using a Post–Column Reaction with Fluoresamine," 1981,J. of Chromatography vol. 218, pp. 3–13.

Trathnigg et al."Two–Dimensional Liquid Chromatography of Functional Polyethers", 1999,Amer.Chem.Soc.Chap. 13,pp. 190–199.

Murphy et al."One– and Two–Dimensional Chromatographic Analysis of Alcohol Ethoxylates", 1998, Analytical Chemistry vol. 70, pp. 4353–4360.

Murphy et al.,"Effect of Sampling Rate on Resolution in Comprehensive Two–Dimensional Liquid Chromatography"1998,Anal. Chem. 70, pp.1585–1594.

Poche et al."Use of Laboratory Robotics for Gel Permeation Chromatography Sample Preparation:Automation of High–Temperature Polymer Dissolution",1997, J.Appl.Polym.Sci.64(8),pp. 1613–1623.

Petro et al."Polymers Immobilized on Silica Gels as Stationary Phases for Liquid Chromatography",1993,Chromatographia 37(9–10), pp. 549–561.

Gilson Advertisement for Multiple Probe with 889 Injection Module.

Petro et al.,"Molded Monolithic rod of macroporous Poly-(styrene–co–divinylbenzene(:) as a Separation Medium for HPLC of Synthetic Polymers:"on–column"Precipitation–Redisolution Chromatography as an Alternative to size Exclusion Chromatography of Styrene Oligomers and Polymers", 1996,Ana. Chem.68,pp. 315–321.

Rassi et al.,"High Performance Liquid Chromatography of Glycoconjugates", 1998,Macromol. Chem., Macromol. Symp.17,pp. 305–319.

Renn et al., "High Speed And Super–Speed Size–Exclusion Chromatography of Polymers for Process Analysis", 1988, Anal.Chem., vol. 60, pp. 200–204.

Revillon et al.,"Capillary Hydrodynamic Chromatography: Optimization Study", 1989,J.Appl.Poly.Sci. vol. 43, pp. 115–128.

Stulik,"Electrochemical detection for flow analysis and liquid chromatography", present status and some roads to the future, 1993,Analytica Chemica Acta. 273,pp. 435–441.

Taylor et al.,"Development of a Flow Injection Analysis Method for the Determination of Acrylamide Copolymers in Brines", 1998,J.Petroleum Sci. and Eng. 21,pp. 129–139.

Taylor et al.,"Development of a Flow Injection Analysis Method for the Determination of Acrylamide Copolymers in Olfield Brines", 1995,SPE Symposium 29009, pp. 691–700.

Tessema et al.,"Simultaneous amperometric determination of some mono–.di–, and oligosacchrides in flow injection and liquid chromatography using two working enzyme electrodes with different selectivity" 1997. Analytica Cehmica Acta.349,vol. 179–188.

Trumbore et al.,"Further experiments on a new, fast method for determining molecular weights of diffusing species in a liquid phase", 1985,J.Chromatography 322,pp. 443–454.

Ui,N.,"High–Speed Gel Filtration of Glycopolypeptides in 6M Guanikine Hydrochloride", 1981,J.Chromatography 215,pp. 289–294.

Monning et al.,"Sample Gating In Open Tubular and Packed Capillaries for High–Speed Liquid Chromatography",1991, Amer. Chem. Soc.,Columbus,vol. 63, pp. 807–810.

Mori,"High–Speed Gel Permeation Chromatography. A Study of Operational Variables", 1977,J.Appl. Ply. Sci.,vol. 21, pp. 1921–1932.

Nielsen et al.,"The Preparation and Rapid Screening of Combinatorial Polymer Libraries", 1999,Amer. Chem. Soc., PMSE 80, p. 92.

Olson et al.,"Dynamic Surface Tension and Adhesion Detection for the Rapid Analysis of Surfactants in Flowing Aqueous Liquids", 1997,Anal. Chem., vol. 69, pp. 3496–3505.

Ouano,"Gel Permeation Chromatography VII. Molecular Weight Detection of GPC Effluents", 1973,J.Polymer Csi: Symposium, vol. 43, pp. 299–310.

Peters et al.,"Molded Rigid Polymer Monoliths as Separation Media for Capillary Electrochromatography.2.Effect of Chromatographic Conditions on the Separation", 1998, Anal.Chem 70, pp. 2296–2302.

Petro et al.,"Chromatography of functional Polymers: A New Approach to the Characterization of Reactive Polymers Obtained by Chemical Modification", 1997,J.Polym. Sci. A: Polym. Chem. 35,pp. 1173–1180.

Petro et al.,"Immobilization of Trypsin onto "Molded" macroporous Poly(Glycidyl Methacrylate–on–Ethylene Dimethacrylate) Rods and Use of the Conjugates as Biocreaters and for Affinity Chromatography",1996,Biotech. And BioEng.pp. 355–363.

Petro et al,"Molded continuous poly rod as a separation medium for the very fast separation of polymers comparison of the chromatographic properties of the monolithic rod with columns packed with porous and non–porous beads in high performance liquid chromatography of polystyrenes", I.J.Chromatography A.752,pp. 59–66.

Petro et al.,"Monodisperse Hydrolyzed Poly(glycidyl methacrylate–co–ethylene dimethacrylate) Beads as a Stationary Phase for Normal–Phase HPLC",1997, Amer. Chem. Soc. 69(16), pp. 3131–3139.

Jansen et al.,"Parallel Column Ion Exchange for Post–Separation PH Modification in Liquid Chromatography", 1986, Journal of Chromatography,366,pp. 135–144.

Kato et al,"Chlonde attachment negative–ion mass spectra of sugars by combined liquid chromatography and atmospheric pressure chemical ionization mass spectrometry," 1991,J.Chromatography,562 pp. 81–97.

Kirkland et al.,"New Concept for characterizing Macromolecules:Intrinsic Viscosity Distributions with High–Resolution Separation", 1991,J.Appl. Poly. Sci. 48,pp. 39–59.

Klaener et al.,"Combinatorial Polymer Chemistry", 1999, Amer. Chem. Soc., vol. 40(1), p. 469.

Krull et al.,"Biopolymer Determination by High–Performance Liquid Chromatography With Low Angle Laser Light Scattering Photometry", *Trac Trends in Anal. Chem.,*Cambridge,vol. 8, 1989, pp. 260–268.

Lesec et al.,"Single–Capillary Viscometer Used for Accurate Determination of Molecular Weights and Mark–Houwink Constants", 1993,Amer. Chem. Soc. Chap 14, pp. 220–230.

MacLean,"Polymer Molecular Weight Distribution Analysis at Very High Speed Using On–Line Data Handling", 1974, J.Chromatography,99,pp. 425–433.

Mendichi et al.,Evaluation of a Single–Capillary Viscometer Detector On Line to a SEC System Used with a New Pulse–Free Pump, 1998,J Appl, Poly Sci. 68, pp. 1651–1659.

Mislovicova et al.,"Behaviour of Polyhydroxyethyl methacrylate sorbent with dextran–filled macropores in dye–affinity chromatography of proteins", 1993,J.Chromatography,646, pp. 411–416.

Mislovicova et al,"Effect of Dextran filling in Macroporous Hema Sorbent on its Behavior in Dye–Affinity Chromatography", 1995,J. Liquid Chromatography 18(15), P3061–3075.

Fortheringham et al, "An integrated GPC–SEC system for room–temperature and high–temperature polymer characrerization", American Lab., 1998, pp. 25–32.

Frechet et al.,"Molded Monolithic Columns as an Alternative to SEC Columns for the Very Fast Characterization of Oligomers and Polymers", PSME, 92: 42–43, 1997.

Frechet et al.,"Modified Macroporous Polymer Beads in the Chromatographic Analysis of Chemical Distribution within Functional Polymers", PSME 77:38–39, 1997.

Hallsworth et al.,"A rapid HPC protocol for detection of polyols and trehalose", J. Microbiological Methods 29:7–13, 1997.

Hancock et al.,"Refractive Index Gradient detection of femtomole Quantities of Polymers by Microbore Size–Exclusion Chromatography", American Chem. Soc. Columbus, vol. 60, pp. 1915–1920, 1998.

Hancock et al.,"Rapid Characterization of Linear and Star–Branched Polymers by Concentration Gradient Detection", 1988,Amer. Chem. Soc.,60, pp. 2812–2818.

Hibi et al.,"Semi–Micro Size–Exclusion Chromatography: Molecular Weight Measurement of Poly(ethylene terephthalate) and Seperation of Oligomers and Preepolymers", 1986, Chromatographia 21,pp. 645–641.

Hirayama et al.,"High–speed aqueous gel permeation chromatography using poly (vinyl alcohol) hollow fibre", J. Chromatography, 1986,368, pp. 391–394.

Hunt et al.,"Rapid Molecular Weight Estimation and Separation of Selected Immunoglobulin Chains by High Speed Gel Filtration", 1983,J.Immun. Methods, 65, pp. 199–205.

Opiteck et al."Two–Dimensional SEC/RPLC Coupled to Mass Spectrometry for the Analysis of Peptides"1997,Anal. Chem.vol. 69, pp. 2283–2291.

Goetzinger, W.K.,"Fast Gradient RP–HPLC For High–Throughput Quality Control Analysis of Spatially Addressable Combinatorial Libraries", Amer. Lab,US International Scientific Communications Shelton, vol. 30, 1988,pp. 27–37.

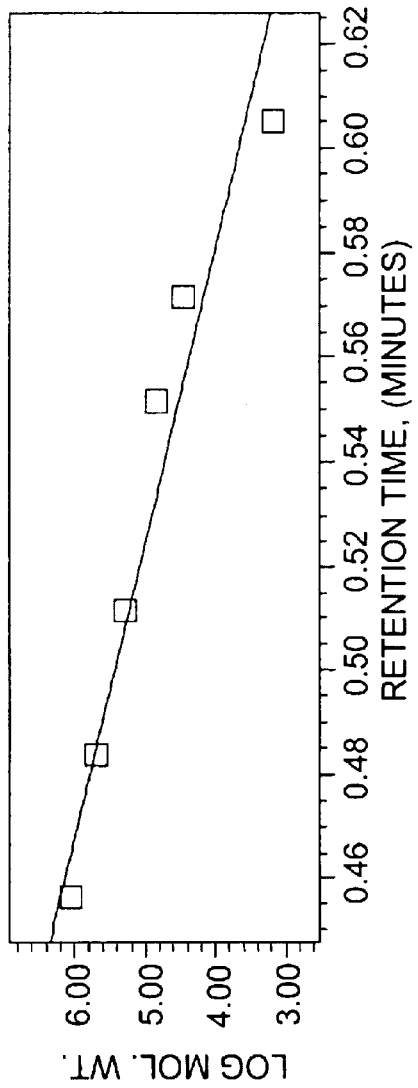
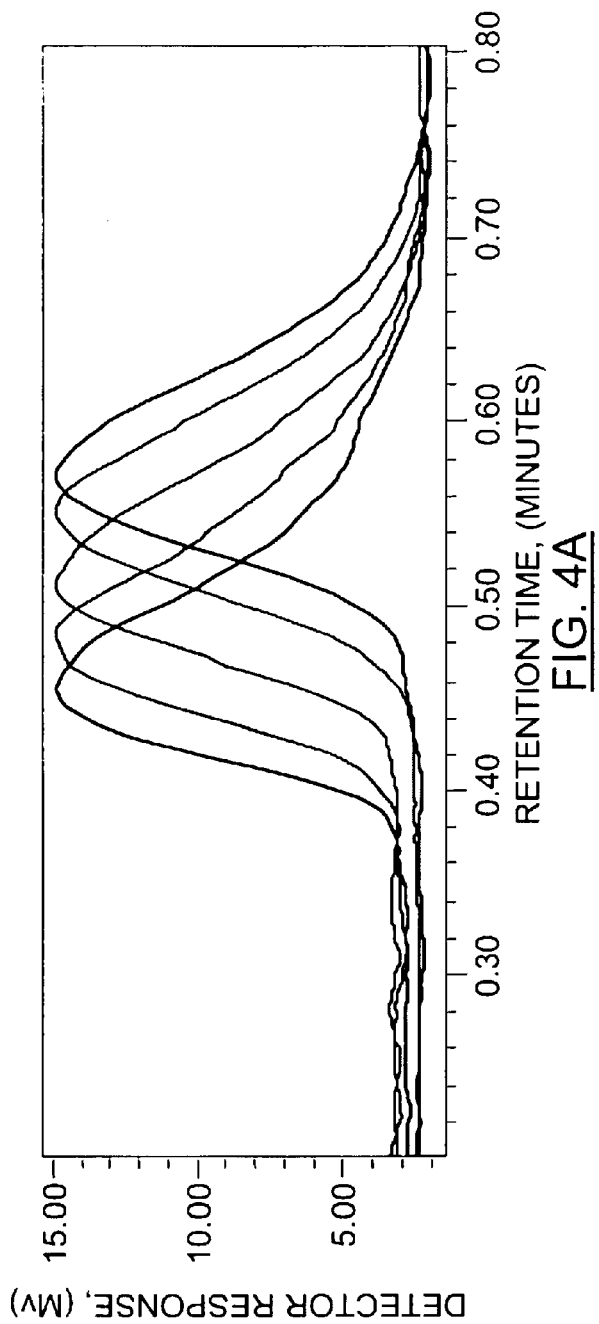
FIG. 4B
FIG. 4A

LIBRARY TYPE: RANDOM COPOLYMERS POLY(AB)

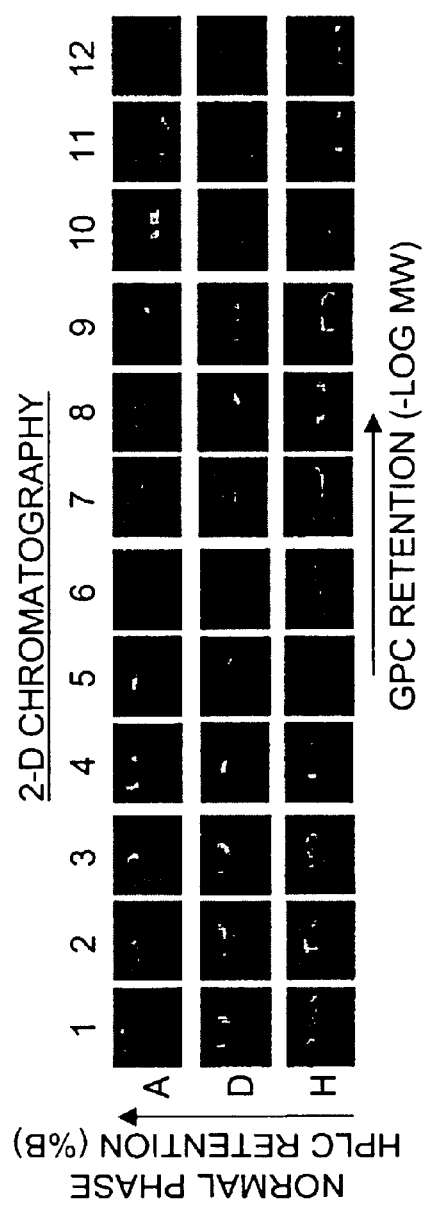
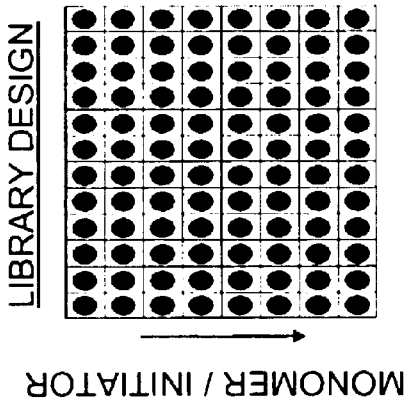
FIG. 8B
FIG. 8C
FIG. 8A

METHODS AND APPARATUS FOR CHARACTERIZATION OF POLYMERS USING MULTI-DIMENSIONAL LIQUID CHROMATOGRAPHY WITH REGULAR SECOND-DIMENSION SAMPLING

CROSS-REFERENCE TO RELATED APPLICATION

This application hereby claims the benefit of now abandoned U.S. provisional application Ser. No. 60/315,685, entitled "Methods and Apparatus for Characterization of Polymers Using Multi-Dimensional Liquid Chromatography," filed Aug. 28, 2001, the disclosure of which is incorporated by reference in its entirety.

BACKGROUND OF INVENTION

The present invention generally relates to methods and apparatus for characterization of polymer samples in liquid chromatography systems, and specifically, for characterization of polymer samples in multi-dimensional liquid chromatography systems. The invention particularly relates, in a preferred embodiment, to characterization of polymer samples in a comprehensive, directly-coupled, multi-dimensional high-performance liquid chromatography systems including a first HPLC dimension adapted for determining composition (e.g., adapted for reverse phase chromatography, adsorption chromatography, and the like such as mobile phase gradient-elution chromatography) and a second HPLC dimension adapted for determining molecular weight or size (e.g., adapted for size exclusion chromatography such as gel permeation chromatography).

Multi-dimensional high-performance liquid chromatography systems are known in the art. See e.g., Murphy et al., *Effect of Sampling Rate on Resolution in Comprehensive Two-Dimensional Liquid Chromatography*, Anal. Chem. 70, 1585–1594 (1998); Murphy et al., *One-and Two-Dimensional Chromatographic Analysis of Alcohol Ethoxylates*, Anal. Chem. 70, 4353–4360 (1998); Kilz et al., *Two Dimensional Chromatography for the Deformulation of Complex Copolymers*, Chapter 17, pp. 223–241 of the text entitled "Chromatographic Characterization of Polymers, Hyphenated and Multidimensional Techniques", edited by Provder et al. (American Chemical Society, Advances in Chemistry Series 247, 1995); Opiteck et al., *Two-Dimensional SEC/RPLC Coupled to Mass Spectrometry for the Analysis of Peptides*, Anal. Chem. 69, 2283–2291 (1997); and Trathnigg et al., *Two-Dimensional Liquid Chromatography of Functional Polyethers*, Chapter 13, pp. 190–199 of the text entitled "Chromatography of Polymers, Hyphenated and Multidimensional Techniques", edited by Provder et al. (American Chemical Society, Symposium Series 731, 1999), each of which is hereby incorporated by reference for all purposes.

Although the methods and systems disclosed to date in the art have proven to be useful for characterizing biological and non-biological polymer samples, they generally suffer from inefficiencies with respect to overall sample throughput, and/or with respect to complicated control and/or operation schemes and systems.

Accordingly, there remains a need in the art for improved methods and systems for effecting multi-dimensional liquid chromatography for characterization of polymer samples.

SUMMARY OF INVENTION

It is therefore an object of the present invention to provide methods and apparatus that allow for more efficient, and relatively less complicated approaches than the prior art for characterizing polymer samples, and especially for fingerprinting polymer samples such as non-biological copolymer samples.

Briefly, therefore, the present invention is directed, generally, to methods for characterizing a polymer sample in a multi-dimensional liquid chromatography system. In preferred embodiments, the invention is directed to methods for characterizing a library of polymer samples in a multi-dimensional liquid chromatography system. The multi-dimensional liquid chromatography system comprises at least a first dimension and a second dimension, and in some embodiments, can include a third dimension, a fourth dimension and/or additional dimensions. Preferably, each of the first dimension and the second dimension is a high-performance liquid chromatography (HPLC) subsystem. The multi-dimension liquid chromatography system is preferably a comprehensive multi-dimension liquid chromatography system wherein at least a portion of each of the sample components separated in the first dimension are further separated into subcomponents in the second dimension. Further, the first dimension and second dimension of the multi-dimensional liquid chromatography system are preferably directly-coupled, wherein the components separated in the first dimension are sampled in near real time (e.g., in-line) as they elute off of the first-dimension chromatography column(s) for injection into the second dimension—for example, through a second-dimension in-line multi-port injection valve.

The method generally comprises, for characterization of a single polymer sample, injecting the polymer sample into a first-dimension high-performance liquid chromatography subsystem, separating the polymer sample into two or more components in the first-dimension liquid chromatography subsystem, optionally detecting a property of the first-dimension separated components in the first-dimension eluent (e.g., using a flow-through detector), sampling at least a portion of each of the first-dimension separated components for directly-coupled injection into a second dimension, injecting each of the sampled portions into a second-dimension high-performance liquid chromatography subsystem, separating at least one of, and preferably each of the sampled portions of the first-dimension separated components into two or more subcomponents in the second-dimension liquid chromatography subsystem, and detecting a property of the second-dimension separated subcomponents in the second-dimension eluent (e.g., using a flow-through detector).

More specifically, for characterizing a single polymer sample, the polymer sample is injected (e.g., using a multi-port injection valve as a first-dimension injector) into a first-dimension mobile phase of a first HPLC dimension of the multi-dimensional liquid chromatography system. At least one sample component of the injected polymer sample is chromatographically separated from other sample components thereof in a first-dimension liquid chromatography column (e.g., in selectable fluid communication with the first-dimension injector), such that a first-dimension mobile phase eluent from the first-dimension column comprises two or more first-dimension separated sample components. Optionally, a property of the first-dimension separated components in the first-dimension mobile phase effluent can be detected using a flow-through detector (e.g. mass detector, universal concentration detector, light-scattering detector, etc.). Then, at least a portion of each of the first-dimension separated sample components from the first-dimension mobile phase eluent are sampled for directly-coupled injection into a second HPLC dimension of the multi-dimensional chromatography system (e.g., using sample loops associated with a multi-port injection valve). The sampled portions of each of the first-dimension separated sample components are then injected directly into a second-dimension mobile phase of the second HPLC dimension of the multi-dimensional liquid chromatography system (e.g., using a multi-port injection valve as a second-dimension injector). At least one subcomponent of the injected sample portions is chromatographically separated from other sub-components thereof in a second-dimension liquid chromatography column (e.g., in selectable fluid communication with the second-dimension injector), such that a second-dimension mobile phase eluent from the second-dimension column comprises two or more second-dimension separated subcomponents for one or more, and in some cases, for each of the sampled portions of each of the first-dimension separated sample components. A property of the second-dimension separated subcomponents are detected in the second-dimension mobile phase effluent using a flow-through detector.

For characterization of a library of polymer samples comprising four or more polymer samples, the aforementioned steps, as generally or specifically characterized, of injecting into the first dimension, separating into components in the first dimension, optionally detecting separated components in the first-dimension eluent, injecting into the second dimension, separating into subcomponents in the second dimension and detecting separated subcomponents in the second-dimension eluent are repeated for each of the polymer samples of the library.

In preferred embodiments, the method is further characterized according to one or more of the following characterizing embodiments, considered independently or in combination in any of the various possible permutations.

In a first characterizing embodiment, at least a portion of each of the first-dimension separated sample components are sampled by repetitively sampling discrete volumes of the first-dimension mobile phase eluent at regularly recurring time intervals. That is, the sampling for the second dimension is effected at regular, recurring intervals of time without regard to whether or not a first-dimension separated component of the sample is present and actually sampled. Advantageously, such an approach is relatively less complicated than other schemes for second-dimension sampling, is robust, and has universal applicability across a wide range of polymers. Moreover, by controlling the separation rates of both the first and second dimensions (e.g., with the overall separation rate being characterized, for example, as the injection rate into the first dimension), together with controlling the second-dimension sampling frequency and sample size, high-resolution multi-dimensional characterization can be effected.

In a second characterizing embodiment, the second-dimension of the multi-dimensional liquid chromatography system is a parallel-column high-performance liquid chromatography subsystem, with serially-selected or parallel detection. More specifically, the second dimension of the multi-dimensional liquid chromatography system comprises two or more parallel second-dimension liquid chromatography columns, and a second-dimension mobile phase is continuously supplied in parallel through the two or more second-dimension liquid chromatography columns. The sampled portions of the first-dimension separated sample components are serially and distributively injected into the second-dimension mobile phases of the two or more second-dimension liquid chromatography columns, respectively. At least one subcomponent of the injected sample portions is then chromatographically separated from other subcomponents thereof substantially simultaneously (i.e., slightly offset temporally) in the respective second-dimension liquid chromatography columns. Advantageously, such an approach provides for substantially improved overall sample throughput, since the multiple second-dimension samples can be substantially simultaneously evaluated, with a relatively uncomplicated mechanical system comprising a single common injector. Moreover, effecting the chromatographic separation step of the second dimension in parallel (i.e., substantially simultaneous separation using two or more second-dimension columns) can advantageously provide a significant improvement of the second dimension resolution by allowing for relatively prolonged second dimension separation times for each of the sampled portions of the first-dimension eluent (as compared to a strictly serial second-dimension chromatographic separation and analysis), while keeping the overall number of second dimension separations the same as can be effected in the serial second-dimension separation. Generally, the operational conditions of the first and second dimensions can be selected to achieve an appropriate balance between the overall sample throughput (in the first and/or second dimension) and the desired resolution.

A third characterizing embodiment is directed to a method for characterizing a library of polymer samples. In this embodiment, a library of polymer samples are provided for characterization in the multi-dimensional liquid chromatography system, with the library comprising four or more different polymer samples for analysis. The multi-dimensional liquid chromatography system comprises a first dimension and a second dimension, with one of the first or second dimensions being adapted for size exclusion chromatography. In a particularly preferred embodiment, the second dimension HPLC subsystem is adapted for size-exclusion chromatography (SEC) such as gel permeation chromatography (GPC). More specifically, in this third characterizing embodiment, at least a portion of each of the first-dimension separated sample components are sampled by sampling at least ten discrete volumes of the first-dimension mobile phase eluent. The steps of injecting a polymer sample into the first-dimension mobile-phase, chromatographically separating the injected polymer in the first dimension, optionally detecting a property of the first-dimension separated components, sampling the first-dimension mobile phase eluent for injection into the second-dimension, injecting into the second dimension, separating in the second dimension, and detecting a property of the second-dimension separated subcomponents are repeated for each of the four or more polymer samples of the library, with the four or more polymer samples of the library being successively injected into the first-dimension mobile phase of the first dimension at intervals of not more than about 30 minutes per sample. In preferred approaches for this embodiment, the injection-to-injection interval is preferably not more than about 15 minutes, and more preferably not more than about 10 minutes.

The present invention is directed as well, to an apparatus for effecting the above-identified methods. That is, the invention is directed as well to multi-dimensional liquid chromatography systems comprising a-first dimension high-performance liquid chromatography subsystem and a second dimension high-performance liquid chromatography subsystem. In general, the first dimension HPLC subsystem comprises a first-dimension mobile phase source in fluid communication with a first-dimension liquid chromatography column, a first-dimension pump in fluid communication with the first dimension mobile phase source and with the first-dimension column for continuously supplying a first-dimensional mobile phase through the first dimension column, an injection valve in selectable fluid communication with the first-dimension mobile phase for serially injecting polymer samples into the first-dimension mobile phase, and optionally, a first-dimension flow-through detector in fluid communication with the first-dimension mobile phase eluent for detecting a property of the first-dimension separated sample component. The second dimension HPLC subsystem comprises a second-dimension mobile phase source in fluid communication with a second-dimension liquid chromatography column, a second-dimension pump in fluid communication with the second dimension mobile phase source and with the second-dimension column for continuously supplying a second-dimensional mobile phase through the second dimension column, a second-dimension injector in selectable fluid communication with the first-dimension mobile phase eluent and in selectable fluid communication with the second-dimension mobile phase for serially sampling at least a portion of the first-dimension separated components from the first-dimension mobile phase eluent and for injecting the sampled portion into the second-dimension mobile phase, and a second-dimension flow-through detector in fluid communication with the second-dimension mobile phase eluent for detecting a property of the second-dimension separated subcomponents.

In preferred embodiments, the multi-dimensional liquid chromatography systems are further characterized according to one or more of the following characterizing embodiments, considered independently or in combination in any of the various possible permutations.

In one characterizing embodiment, the multi-dimensional liquid chromatography system is further characterized as comprising a controller for the second-dimension injector, the controller being adapted for sampling discrete volumes of the first-dimension mobile phase eluent at regularly recurring time intervals, and for injecting the sampled volumes into the second-dimension mobile phase.

In another characterizing embodiment, the multi-dimensional liquid chromatography system is further characterized as having a first-dimension HPLC subsystem comprising a single mobile phase analysis channel, and a second-dimension HPLC subsystem comprising at least two analysis channels in parallel. More specifically, the second-dimension HPLC subsystem comprises at least two second-dimension liquid chromatography columns, and is adapted to continuously supply the second-dimension mobile phase in parallel through the two or more second-dimension liquid chromatography columns (e.g., from the second-dimension mobile phase source). In preferred aspects of this characterizing embodiment, the second-dimension mobile-phase is supplied to each of the second-dimension columns through one or more flow restrictors.

In yet a further characterizing embodiment, the multi-dimensional liquid chromatography system is further characterized as comprising a control system adapted for serially injecting successive polymer samples into the first dimension mobile phase of the system at intervals of not more than about 30 minutes for sample, and adapted for sampling at least ten discrete volumes of the first-dimensional mobile phase eluent, and injecting the at least ten sampled volumes directly into the second dimension mobile phase.

In particularly preferred embodiments, including both method embodiments and apparatus embodiments, the following features can be applied generally with respect to any of the aforementioned embodiments, alone or in combination in the various permutations. Generally, the polymer samples being characterized can be non-biological polymers (e.g., non-biological copolymers) or biological polymers (e.g., proteins, DNA), and in many applications, are preferably non-biological polymers. Generally, the first dimension HPLC subsystem can be adapted for chromatographic approaches effective for distinguishing between chemical composition and/or structural variations of polymer sample components (e.g., repeat units types, ratios of copolymer repeat units, functional groups, branching, etc.). Exemplary preferred first-dimension HPLC subsystems include reverse phase chromatography subsystems, mobile-phase compositional gradient elution chromatography subsystems, or mobile-phase temperature gradient elution chromatography subsystems. Mobile-phase elution gradients of the first dimension preferably comprise a substantially universal co-solvent system, such as a water-tetrahydrofuran-hexane system. Generally, the second dimension HPLC subsystem is preferably adapted for size-exclusion chromatography (SEC) such as gel permeation chromatography (GPC). Additionally, the flow-through detector of the second dimension HPLC subsystem is generally preferably a universal concentration detector or mass detector, such as an evaporative light-scattering detector (ELSD). Further, generally, the first and second dimension liquid chromatography subsystems can be combined with further dimensions, such as third, forth or higher dimensions, and such further dimensions can be liquid-chromatography subsystems, gas-chromatography subsystems, electrophoretic subsystems, electrochromatographic subsystems, field-flow fractionation subsystems, flow-injection analysis subsystems, or other types of polymer characterization systems, such as mass spectrometry.

The methods and apparatus of the invention are particularly useful for characterizing individual polymer samples, or libraries of polymer samples, such as non-biological polymer samples, and especially for characterizing combinatorial libraries of polymers (e.g. synthesized using parallel polymerization approaches). The methods and apparatus of the invention can be advantageously applied for polymer fingerprinting—determining both compositional/structural characteristics as well as molecular size/molecular weight characteristics. The methods and apparatus of the invention can also be used for effective scale up of a polymerization synthesis process, to ensure that the fingerprint of the polymer made by large-scale synthesis process is substantially the same as the polymer made by the smaller scale synthesis process.

The methods and apparatus of the invention can be applied using convention, macro-scale liquid chromatography systems, or alternatively, can be applied in a micro-scale or nano-scale format, such as in microfluidic devices such as lab-on-a-chip liquid microfluidic chromatography devices.

Other features, objects and advantages of the present invention will be in part apparent to those skilled in art and in part pointed out hereinafter. All references cited in the instant specification are incorporated by reference for all purposes. Moreover, as the patent and non-patent literature relating to the subject matter disclosed and/or claimed herein is substantial, many relevant references are available to a skilled artisan that will provide further instruction with respect to such subject matter.

BRIEF DESCRIPTION OF THE DRAWINGS

FIGS. 4A and 4B are graphical data showing the results of a multi-dimensional liquid chromatography calibration. FIG. 4A is a graph showing detector response (mV) versus retention time (min) with clear resolution of polystyrene standards subcomponents of different molecular weights. FIG. 4B is a graph showing the corresponding log molecular weigh data versus retention time (min) with the expected substantially linear relationship between components of the polystyrene standards sample.

FIG. 5A is a 3-dimensional plot showing detector response (V) versus both (i) normal-phase HPLC retention time (min), corresponding to the first-dimension separation, and (ii) GPC retention time (min), corresponding to the second-dimension separation, with clear resolution of the various types of polymer components in the polymer sample. FIG. 5B is a 2-dimensional contour graph showing the corresponding top-down view of the data presented in FIG. 5A, including normal-phase HPLC retention time (min), corresponding to the first-dimension separation versus GPC retention time (min), corresponding to the second-dimension separation, again showing clear resolution of the various types of polymer components.

FIG. 7B is a 3-dimensional plot showing molecular weight, as determined from second-dimension GPC data versus polystyrene standard calibration, versus spatial position in the microtiter-format parallel reactor (columns 1–12 and rows 1–7). FIG. 7C is a 3-dimensional plot showing chemical composition, as determined from first-dimension normal phase HPLC data (and shown as % of monomer B incorporated into each of the random copolymer samples), versus spatial position in the microtiter-format parallel reactor (columns 1–12 and rows 1–7).

FIGS. 8A through 8C are graphical representations of the library design for a library of polymer samples (FIG. 8A), the results of a multi-dimensional liquid chromatography experiment (FIG. 8B), and the overlaid results of two separate, independent one-dimensional HPLC characterization experiments (FIG. 8C). Specifically, FIG. 8B is an array of 2-dimensional contour graphs, each graph representing data from one of the samples of the library, and each graph showing chemical composition distribution (represented as normal phase HPLC retention time, corresponding to the relative amount of monomer B in each of the samples), versus molecular weight distribution (represented as GPC retention time (-log MW). FIG. 8C shows the results of the independent, one-dimensional analysis for the same polymer samples for which data is shown in FIG. 8B, and is an array of 2-dimensional plots, each plot representing the combined, independently-obtained data from one of the samples of the library, and each plot showing chemical composition (represented as the relative amount of monomer B in each of the samples as determined by the independent, one-dimension normal phase HPLC gradient elution characterization), versus molecular weight (represented as GPC log MW.

FIG. 9A is a 2-dimensional contour graph showing normal-phase HPLC retention time (sec), corresponding to the first-dimension separation, versus GPC retention time (min), corresponding to the second-dimension separation, with clear resolution of the polymer components. FIG. 9B is a plot showing the data from the GPC-FTIR.

DETAILED DESCRIPTION OF THE INVENTION

Figure 1:
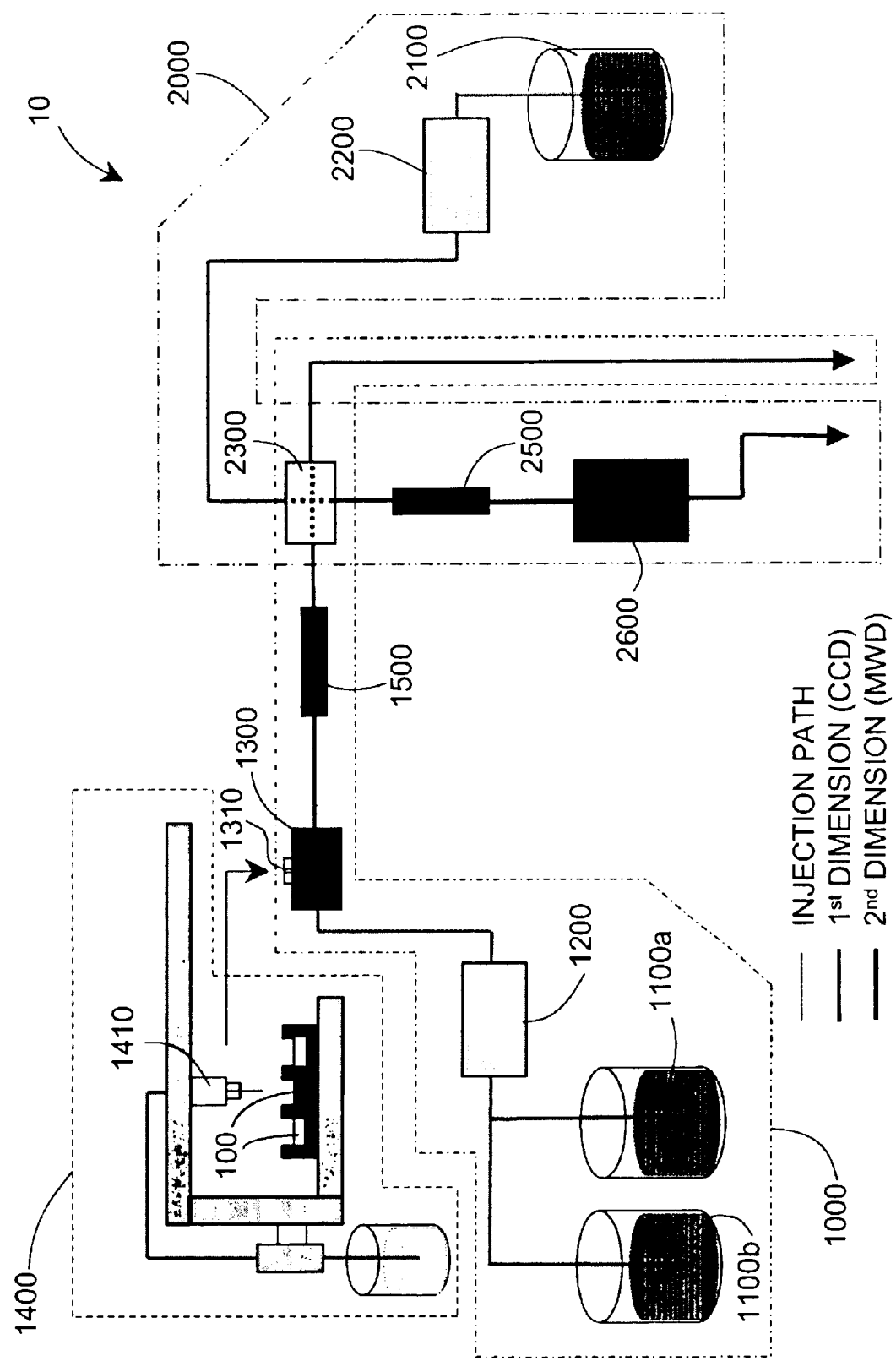
FIG. 1 is a schematic representation of a multi-dimensional liquid chromatography system.

In the present invention, methods and apparatus are disclosed for characterization of single polymer samples and/or for characterization of a library comprising four or more polymer samples. Preferably, the characterization methods and apparatus can be applied for fingerprinting biological and non-biological polymer samples—for analysis in an analytical laboratory, or for analysis in an on-line, near real time process monitoring or process control system.

Certain characterizing features of this invention are related to inventions described in co-owned U.S. patent applications, including (i) U.S. Ser. No. 09/710,801, (now U.S. Pat. No. 6,406,632), entitled "Rapid Characterization of Polymers," filed Nov. 8, 2000 by Safir et al., as a continuation application of U.S. Ser. No. 09/285,363, filed Apr. 2, 1999 (now abandoned), which itself claimed the benefit of U.S. provisional application Ser. No. 60/080,652, filed Apr. 3, 1998 (the application Ser. No. 09/710,801 being hereinafter referred to as the "Co-Owned Rapid Characterization of Polymers Application"), and (ii) U.S. Ser. No. 09/410,546, (now U.S. Pat. No. 6,296,771), entitled "Parallel High-Performance Liquid Chromatography with Serial Injection," filed Oct. 1, 1999 by Petro et al, as a continuation-in-part application of the following applications: U.S. Ser. No. 09/285,363, U.S. Ser. No. 09/285,393 (now U.S. Pat. No. 6,265,226), U.S. Ser. No. 09/285,333 (now U.S. Pat. No. 6,260,407), U.S. Ser. No. 09/285,335 (now U.S. Pat. No. 6,175,409), and U.S. Ser. No. 09/285,392 (now U.S. Pat. No. 6,294,388), each of which themselves claimed the benefit of U.S. provisional application Ser. No. 60/080,652, filed Apr. 3, 1998 (the Ser. No. 09/410,546 being hereinafter referred to as the "Co-Owned Parallel HPLC Application"). Each of the aforementioned co-owned U.S. patent applications (i.e., the Co-Owned Rapid Characterization of Polymers Application and the Co-Owned Parallel HPLC Application) are hereby incorporated by reference for all purposes. Many features of the present invention will be described hereinafter with reference to the Co-Owned Rapid Characterization of Polymers Application and/or the Co-Owned Parallel HPLC Application.

The invention is described in further detail below with reference to the figures, in which like items are numbered the same in the several figures.

A multi-dimensional liquid chromatography system of the present invention comprises a first dimension liquid chromatography subsystem, and a second dimension liquid chromatography subsystem, and optionally, third dimension and/or fourth dimension and/or additional dimension subsystems. Although the first dimension and second dimension are liquid chromatography subsystems, and preferably high-performance liquid chromatography subsystems, the additional dimension subsystems can be liquid chromatography subsystems, gas chromatography subsystems, electrophoretic subsystems, electrochromatographic subsystems, field-flow fractionation subsystems, flow-injection analysis subsystems or other types of polymer characterization subsystems, including for example, mass spectrometry.

Referring to FIG. 1, the multi-dimensional liquid chromatography system 10 can include a first dimension HPLC subsystem 1000 and a second dimension HPLC subsystem 2000. In general, the first dimension HPLC subsystem 1000 comprises a first-dimension mobile phase source (e.g., as shown, in one or more mobile phase reservoirs) 1100a, 1100b in fluid communication with a first-dimension liquid chromatography column 1500. A first-dimension pump 1200 provides fluid communication between the first dimension mobile phase source 1100a, 1100b and with the first-dimension column 1500 for continuously supplying a first-dimensional mobile phase through the first dimension column 1500. The first dimension HPLC subsystem 1000 further comprises an injection valve 1300, that can include an injection port 1310 for receiving polymer samples from a sample source (e.g., such as a sample handling robot 1410 of polymer sampling system 1400, or from an on-line sampling system in a polymerization process line, not shown). The first-dimension injection valve 1300 is in selectable fluid communication with the first-dimension mobile phase for serially injecting polymer samples 100 into the first-dimension mobile phase. Although not shown in FIG. 1, the first dimension HPLC subsystem can optionally further include a first-dimension flow-through detector in fluid communication with the first-dimension mobile phase eluent for detecting a property of the first-dimension separated sample component. First-dimension mobile phase eluent is, as discussed in further detail below, discharged through a second-dimension sampling and injection system (generally referred to herein as a second-dimension injector) and/or to an exhaust or waste port or collection reservoir.

With further reference to FIG. 1, the second dimension HPLC subsystem 2000 comprises a second-dimension mobile phase source 2100 in fluid communication with a second-dimension liquid chromatography column 2500. A second-dimension pump 2200 provides fluid communication between the second dimension mobile phase source 2100 and with the second-dimension column 2500 for continuously supplying a second-dimensional mobile phase through the second dimension column 2500. A second-dimension injector 2300 is in selectable fluid communication with the first-dimension mobile phase eluent for serially sampling at least a portion of the first-dimension separated components from the first-dimension mobile phase eluent. The sampling is generally effected in discrete volumes, as further discussed below. The second-dimension injector 2300 is also in selectable fluid communication with the second-dimension mobile phase for injecting the sampled portion (e.g., the discrete sampled volumes taken from the first-dimension mobile phase eluent) into the second-dimension mobile phase. The second-dimension injector 2300 can also include additional hardware, such as flow-splitters, for changing the concentration and/or flow rate of the sampled portion of the first-dimension eluent. The second dimension HPLC subsystem further comprises one or more second-dimension flow-through detectors 2600 in fluid communication with the second-dimension mobile phase eluent for detecting a property of the second-dimension separated subcomponents.

The first dimension HPLC subsystem 1000 and the second dimension HPLC subsystem 2000 of the multi-dimensional liquid chromatography system 10 are preferably directly-coupled, wherein components of the polymer sample 100 separated in the first dimension are sampled in near real time (e.g., in-line) from the first-dimension eluent as they elute off of the first-dimension chromatography column(s). The sampled first-dimension separated components (or one or more portions thereof) are then injected into the second dimension—for example, through a second-dimension injector 2300. Preferably, the second-dimension injector 2300 is an integral second-dimension injector 2300 that is functionally a component of the both the first-dimension subsystem 1000 and the second-dimension subsystem 2000—and is adapted for both sampling and injecting. The sampling and injection functions could, however, be accomplished using non-integral components, provided as separate system components, and linked for example, manually or using robotic transfer (not shown). Such a non-integral second-dimension sampling and injection system is still considered to be directly coupled, provided that there is no long term storage of the sampled portions of the first-dimension eluent prior to injection into the second-dimension eluent. Preferably, the discrete volumes sampled from the first dimension eluent are not stored at all, and are injected immediately, in sequential steady state operation, into the mobile phase of the second dimension. It is, nonetheless, contemplated that some built-in time delay could be incorporated into the method to allow for treatment of the sampled portion prior to injection into the second-dimension mobile phase. For example, sampled portions of the first-dimension mobile phase eluent could be stored (e.g., for treatment or otherwise) for not more than about 4 hours, preferably not more than about 2 hours, more preferably still not more than about 1 hour, and still more preferably not more than about 30 minutes, 10 minutes, 5 minutes, 2 minutes, 1 minute, 30 seconds, 15 seconds, 10 seconds or 5 seconds. As noted, the second-dimension injector 2300 could also include additional functionality, such as flow-splitting for changing the concentration and/or flow rate of the sampled portion of the first-dimension eluent.

Figure 2:
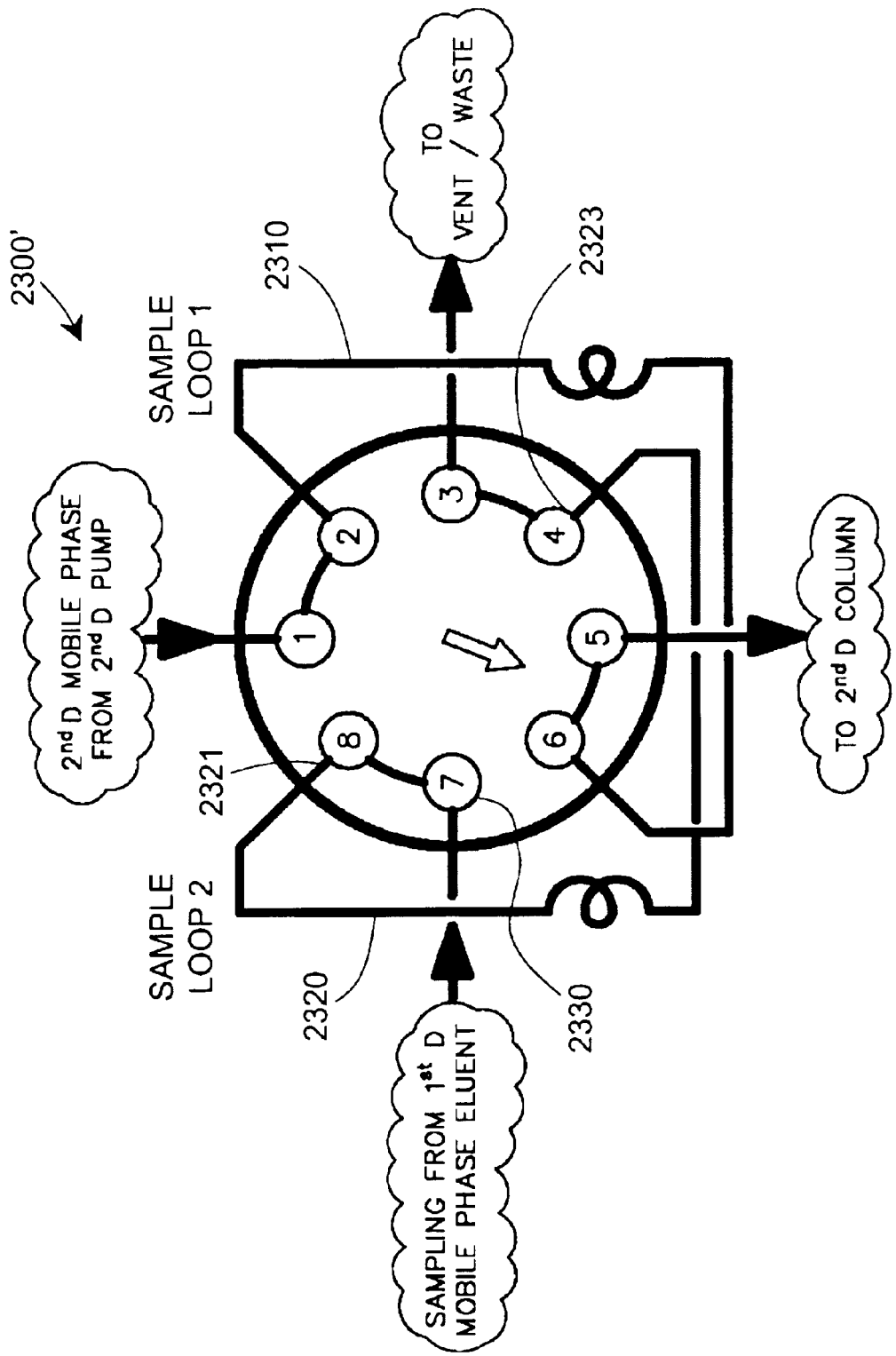
FIG. 2 is a schematic representation of a multi-port injection valve having two sample loops suitable for use as a second-dimension injector in the multi-dimensional liquid chromatography system of FIG. 1.

Referring now to FIG. 2, in many embodiments, the second-dimension injector 2300 can be a multi-port injection valve 2300', preferably comprising one or more sample loops 2310, 2320. Operation of such multi-port injection valves are discussed in detail in the Rapid Characterization of Polymers Application. Briefly, in a first switch position and valve configuration depicted in FIG. 2, the first dimension mobile phase eluent is discharged into an inlet port 2330 of the injection valve 2300'. The first switch position and valve configuration allows for the first-dimension eluent to pass through a inlet 2321 of the sample loop 2320, through the sample loop 2320, and through an outlet 2323 thereof to waste, thereby loading the sample loop 2320. Meanwhile, the second-dimension mobile phase is being routed through the other sample loop 2310 to the second dimension column 2500. When the switch position and valve configuration is switched to an alternative second switch position and valve configuration (not shown), the inlet 2321 of the sample loop 2320 is aligned with the second dimension mobile phase coming from the second dimension pump 2200, and the outlet 2323 of the sample loop 2320 is aligned for fluid communication with the second-dimension column 2500, such that a discrete volume sample equal to the volume of the sample loop 2320 is injected into the second-dimension mobile phase. Repeated alternation between the first and second switch positions/valve configurations allows for alternating loading of sample loops 2310, 2320 and injecting of corresponding discrete sample volumes into the second dimension mobile phase.

Other types of injection valves can be used, including for example, arrays of microvalves configured for sampling and injection, for example, analogous to that described in co-pending U.S. patent application Ser. No. 60/274,022 entitled "Gas Chromatograph Injection Valve Having Microvalve Array" filed Mar. 7, 2001 by Bergh et al, which is hereby incorporated by reference for all purposes.

In operation, with further reference to FIGS. 1 and 2, for characterization of a single polymer sample, a polymer sample 100 is injected into a first-dimension high-performance liquid chromatography subsystem 1000 through first dimension injector 1300. The polymer sample 100 is separated into two or more components in the first-dimension liquid chromatography column 1500, with the two or more components being discharged from the column 1500 as part of the first dimension mobile phase eluent. Optionally, a property of the first-dimension separated components in the first-dimension eluent can be detected (e.g., using a flow-through detector). At least a portion of the first-dimension separated components are sampled, for example, using the second-dimension injector 2300 for directly-coupled injection into the second dimension HPLC subsystem 2000. The sampled portions of the first-dimension separated components are separated into two or more subcomponents in the second-dimension liquid chromatography columns 2500, and discharged therefrom as part of the second-dimension mobile phase eluent. A property of the second-dimension separated subcomponents is detected in the second-dimension eluent (e.g., using a flow-through detector 2600). For characterization of a library of polymer samples comprising four or more polymer samples, the aforementioned steps of injecting into the first dimension, separating into components in the first dimension, optionally detecting separated components in the first-dimension eluent, injecting into the second dimension, separating into subcomponents in the second dimension and detecting separated subcomponents in the second-dimension eluent are repeated for each of the polymer samples of the library.

The multi-dimension liquid chromatography system is preferably a comprehensive multi-dimension liquid chromatography system wherein at least a portion of each of the sample components separated in the first dimension are further separated into subcomponents in the second dimension. Preferably, the separation rates of the first dimension, the separation rates of the second dimension, the sampling interval (i.e., sampling frequency) for sampling of the first-dimension mobile phase eluent and/or the sampling volume of the sampled portions of first-dimension mobile phase eluent are controlled, independently, in various combinations and/or in combination with other factors, such that at least two discrete fractions of each of the first-dimension separated sample components are sampled. More preferably, such factors are controlled such that at least three discrete fractions, and in some applications, even higher numbers of discrete fractions such as at least four discrete fractions, at least five discrete fractions or at least six discrete fractions of each of the first-dimensions separated sample components are sampled.

Certain preferred characterizing embodiments of the invention are described as follows. These embodiments can be applied individually, or in various combinations, including each of the various permutations thereof. Moreover, certain more general features of the invention, that can be commonly applied to each of these preferred characterizing embodiments or the various possible combinations thereof, are also described hereinafter. As noted, reference is made as appropriate to the aforementioned co-owned related applications, namely the Co-Owned Rapid Characterization of Polymers Application and the Co-Owned Parallel HPLC Application.

Regularly-Recurring 2nd Dimension Sampling Interval

In one preferred embodiment, at least a portion of each of the first-dimension separated sample components are sampled by repetitively sampling discrete volumes of the first-dimension mobile phase eluent at regularly recurring time intervals. That is, the sampling for the second dimension is effected at regular, recurring intervals of time without regard to whether or not a first-dimension separated component of the sample is present and actually sampled. Hence, the multi-dimensional liquid chromatography system can be further characterized as comprising one or more controllers, including for example, controllers for controlling the separation rate of each of the first dimension and second dimension, and especially in particular, a controller for the second-dimension injector, the second-dimension injector controller being adapted for sampling discrete volumes of the first-dimension mobile phase eluent at regularly recurring time intervals, and for injecting the sampled volumes into the second-dimension mobile phase.

In general, the time interval that defines the sampling frequency for sampling the first-dimension mobile phase eluent, and preferably, that also defines the injection frequency of the sampled portion into the second-dimension mobile phase, is not narrowly critical, and can range, for example, from about 10 minutes to about 5 seconds or less. Preferably, the time interval that defines the sampling frequency can range from about 5 minutes to about 10 seconds, and in some embodiments, from about 2 minutes to about 30 seconds. Generally, therefore, a discrete volume of the first-dimension mobile phase is sampled (and preferably, also injected into the second-dimension mobile phase) at least once every 10 minutes, and more preferably at least once every 5 minutes, and most preferably at least once every 2 minutes. In some embodiments, a discrete volume of the first-dimension mobile phase can be sampled (and preferably, also injected into the second-dimension mobile phase) at least once every 180 seconds, and more preferably at least once every 1 minute, even more preferably at least once every 30 seconds, and in some cases, at least once every 15 seconds, at least once every 10 seconds or at least once every 5 seconds.

The sampled volume from the first-dimension mobile phase eluent is likewise not narrowly critical, and can vary depending on the nature and/or goals of the analysis. In preferred applications, for example, the sampled volume can range from about 5 ml to about 5 $\mu$l, preferably from about 1 ml to about 10 $\mu$l and more preferably from about 500 $\mu$l to about 25 $\mu$l. Generally, therefore, the sampled volumes of first-dimension mobile phase eluent are preferably not more than about 5 ml, preferably not more than about 1 ml, and more preferably not more than about 500 $\mu$l. In some embodiments, the sampled volumes of first-dimension mobile phase eluent can be not more than about 250 $\mu$l, not more than about 100 $\mu$l, not more than about 50 $\mu$l, not more than about 25 $\mu$l, not more than about 10 $\mu$l, or not more than about 5 $\mu$l, or not more than about 1 $\mu$l. Such smaller volume samples for second-dimension characterization can have applications, for example, in micro-scale and nano-scale multi-dimensional chromatography systems, such as lab-on-a-chip type systems.

The absolute number of discrete sample volumes sampled from the first-dimension mobile phase eluent for injection into the second-dimension mobile phase can, for each polymer sample being characterized, vary widely depending on the nature and/or goals of the analysis. In many embodiments, for example, the number of discrete volumes of the first-dimension eluent that are sampled (for each polymer sample being characterized) can range from about 5 to about 5000, preferably from about 10 to about 1000, and more preferably from about 20 to about 500, and in some embodiments, from about 100 to about 400. Generally, therefore, the number of discrete volumes of the of the first-dimension eluent that are sampled (for each polymer sample being characterized) is preferably at least about 5, more preferably at least about 10, even more preferably at least about 20, and in some embodiments, at least about 50, at least about 100, at least about 200, at least about 400, at least about 500, at least about 1000, or at least about 5000 or more.

In a particularly preferred approach of this preferred embodiment—in which at least a portion of each of the first-dimension separated sample components are sampled by repetitively sampling discrete volumes of the first-dimension mobile phase eluent at regularly recurring time intervals—the sampling frequency from the first-dimension mobile phase eluent, and/or the injection frequency to the second-dimension, together with the sampled volumes can be controlled, in combination, such that substantially all of the first-dimension mobile phase eluent coming off of the first-dimension column is sampled and subsequently injected into a second-dimension mobile phase for second-dimension analysis. Preferably, the amount of the first-dimension mobile phase eluent coming off of the first-dimension column that is sampled and subsequently injected into a second-dimension mobile phase for second-dimension analysis is at least about 70% or more, and in some embodiments, can be at least about 80%, at least about 90%, at least about 95%, at least about 97% or at least about 99%. Such an approach can substantially approximate a completely-coupled, continuously-coupled and directly-coupled multi-dimensional liquid chromatography system. In a preferred embodiment, for example, at least ten discrete volumes of the first-dimension mobile phase eluent are sampled with a sampling frequency of at least once every 30 seconds, with the sampled volumes being not more than about 250 $\mu$l. If for example, the first-dimension mobile phase flow rate in such a system is about 0.5 ml/min, and the sampling frequency in this system is, in fact, about once every thirty seconds, with a sampled volume of about 250 $\mu$l, then all of the first-dimension mobile-phase eluent is sampled and preferably also injected into the second dimension mobile phase. As another example, with the same first dimension flow rate (0.5 ml/min) and sampling frequency (2 times/minute), if the sampled volume were only about 200 $\mu$l, then about 80% of the total first-dimension mobile phase eluent volume would be sampled into the second dimension. As a further example, with the same first dimension flow rate (0.5 ml/min), but with a higher sampling frequency (4 times/minute), and with a smaller sampled volume (about 100 $\mu$l), then about 80% of the total first-dimension mobile phase eluent volume would again be sampled into the second dimension.

In the directly-coupled, regularly recurring sampling embodiments described above, particularly where the first dimension and second dimension are completely, and continuously coupled (e.g., with relatively small sample volumes), at least one of the sampled volumes of the first-dimension mobile phase eluent may consist essentially of the first-dimension mobile phase, and have an essential absence of first-dimension separated sample components.

$2^{nd}$-Dimension Analysis with Parallel Chromatographic Separation

In another preferred embodiment, the second-dimension of the multi-dimensional liquid chromatography system is adapted for parallel, or at least substantially parallel chromatographic separation of the sampled portions of the first-dimension separated components. That is, the second-dimension subsystem of the invention can be a parallel-column high-performance liquid chromatography subsystem, preferably with a single, common second-dimension injector. More specifically, in this preferred embodiment, the multi-dimensional liquid chromatography system includes a first-dimension HPLC subsystem comprising a single mobile phase analysis channel, and a second-dimension HPLC subsystem comprising at least two analysis channels in parallel, preferably directly coupled through a single, common second-dimension injector. The second dimension HPLC subsystem comprises two or more parallel second-dimension liquid chromatography columns adapted such that a second-dimension mobile phase is continuously supplied in parallel through the two or more second-dimension columns. (e.g., from the second-dimension mobile phase source). In one embodiment, a second-dimension mobile phase can be continuously supplied in parallel to the two or more second-dimension liquid chromatography columns through two or more supply conduits, each of the two or more supply conduits providing continuous parallel fluid communication between a second-dimension liquid mobile-phase source and the two or more second-dimension liquid chromatography columns. In preferred aspects of this embodiment, the fluid communication path to each of the two or more second-dimension columns includes one or more flow restrictors associated with each supply conduit. Further details regarding the flow restrictors, and other aspects of this embodiment are substantially as described in the Co-Owned Parallel HPLC Patent Application.

In a particularly preferred approach for this embodiment—an approach employing a single, common second-dimension injector for coupling the first and second dimension—the sampled portions of the first-dimension separated sample components are serially and distributively injected into the second-dimension mobile phases of the two or more second-dimension liquid chromatography columns, respectively. At least one subcomponent of the injected sample portions is then chromatographically separated from other subcomponents thereof substantially simultaneously (i.e., slightly offset temporally) in the respective second-dimension liquid chromatography columns (as compared between second-dimension columns).

Coupled sampling between the first-dimension and second-dimension subsystems can be effected, as described above, such that a portion of the first-dimension separated components are sampled for injection into the second-dimension mobile phases at regularly recurring time intervals. In an alternative approach, however, the coupling can also be a controlled coupling. Specifically, a portion of the first-dimension separated components can be sampled for injection into the second-dimension mobile phases at intervals triggered by a control signal based on detection of the first-dimension separated components in the first-dimension mobile phase eluent.

Detection in the second dimension can generally be effected serially (e.g., with a selection valve for directing the two or more second-dimension mobile phase eluents to a detector) or in parallel. In parallel second-dimension detection embodiments, each of the two or more chromatographic columns can have its own dedicated detector, such that detection of subcomponents derived from different sampled portions of the first-dimension eluent occurs substantially simultaneously as compared between different analysis channels of the second dimension. For any given sampled component (or portion thereof) of the first-dimension, however, once injected into a particular analysis channel of the second dimension, detection of properties of the second-dimension separated subcomponents is effected serially within that analysis channel. The second dimension detector is preferably an optical detector. An optical detector can be advantageous applied, particularly in highly parallel systems, and/or in systems designed to be effective for nano-scale and/or micro-scale analysis (e.g., lab-on-a-chip applications). An optical detector, such as a light-scattering detector or other optical detector, can be applied directly to samples that can be detected by the optical detector. In some cases, however, the detectability of the sampled separated subcomponents can be developed, for example, by treating second-dimension separated subcomponents to change an optical property thereof before detection with an optical detector.

The number of parallel second-dimension chromatographic columns, and associated second-dimension mobile phases is not of crucial significance, but is preferably four or more second-dimension chromatographic columns, and more preferably eight or more second-dimension chromatographic columns. Higher numbers can also be employed, as described for example in the Co-Owned Parallel HPLC Application.

In one preferred characterization protocol of this embodiment, injection into the second-dimension mobile phase is effected by a second-dimension injection system comprising the second-dimension injector and a multi-port switching valve. The injector has a sample-loading port for serially receiving a plurality of sampled portions and has a sample-discharge port for discharging the plurality of sampled portions under pressure to the switching valve. The switching valve can have an inlet port and two or more selectable outlet ports, the inlet port being in fluid communication with the sample-discharge port of the injector and being in selectable fluid communication with the two or more selectable outlet ports, the two or more selectable outlet ports being in fluid communication with the two or more second-dimension chromatography columns, respectively, such that the sampled portions can be serially and distributively injected into the second-dimension mobile phases of the two or more second-dimension liquid chromatography columns. In a particularly preferred variation of this preferred protocol, in which at least ten portions of the first-dimension mobile phase eluent are sampled, the second-dimension injector is a multi-port switching valve having at least two sample loops, and the second-dimension multi-port switching valve is controlled such that a first sampled portion is injected into a mobile phase of the first column, a second sampled portion is injected into a mobile phase of the second column, a third sampled portion is injected into a mobile phase of the third column, a fourth sampled portion is injected into a mobile phase of the fourth column, a fifth sampled portion is injected into a mobile phase of the first column, a sixth sampled portion is injected into a mobile phase of the second column, a seventh sampled portion is injected into a mobile phase of the third column, an eighth sampled portion is injected into a mobile phase of the fourth column, a ninth sampled portion is injected into a mobile phase of the first column, and a tenth sampled portion is injected into a mobile phase of the second column.

In another preferred protocol, especially where the second dimension of the multi-dimensional liquid chromatography systems comprises four or more parallel second-dimension liquid chromatography columns, the method can be directed to characterizing a provided library comprising ten or more different polymer samples, where the polymer samples are polymerization product mixtures resulting from polymerization reactions that are varied with respect to reaction conditions, reactants, catalysts, catalyst precursors, initiators, additives or the relative amounts thereof. The ten or more polymer samples are serially injected into the first-dimension mobile phase through a first-dimension injector, and a continuously supplied mobile phase is provided in parallel through the four or more second-dimension liquid chromatography columns. The sampled portions of the first-dimension separated components of ten or more polymer samples are serially and distributively injected into the second-dimension mobile phases of the four or more chromatographic columns through a common second-dimension injector.

The number of sampled volumes for second-dimension analysis, the volume thereof, and the second-dimension sampling frequency can be the same as described above in connection with the regularly-recurring second-dimension injection interval embodiment.

Further detailed description of the second-dimension parallel HPLC subsystem, both apparatus and operational aspects thereof is set forth below, in the Co-Owned Parallel HPLC Application.

High-Throughput 2-Dimensional Chromatography with One SEC Dimension

A further preferred embodiment is directed to a method for characterizing a library of polymer samples. In this embodiment, a library of polymer samples are provided for characterization in the multi-dimensional liquid chromatography system, with the library comprising four or more different polymer samples for analysis. The multi-dimensional liquid chromatography system comprises a first dimension and a second dimension, with one of the first or second dimensions being adapted for size exclusion chromatography. In a particularly preferred embodiment, the second dimension HPLC subsystem is adapted for size-exclusion chromatography (SEC) such as gel permeation chromatography (GPC).

More specifically, in this embodiment, at least a portion of each of the first-dimension separated sample components are sampled by sampling at least ten discrete volumes of the first-dimension mobile phase eluent. The steps of injecting a polymer sample into the first-dimension mobile-phase, chromatographically separating the injected polymer in the first dimension, optionally detecting a property of the first-dimension separated components, sampling the first-dimension mobile phase eluent for injection into the second-dimension, injecting into the second dimension, separating in the second dimension, and detecting a property of the second-dimension separated subcomponents are repeated for each of the four or more polymer samples of the library, with the four or more polymer samples of the library being successively injected into the first-dimension mobile phase of the first dimension at intervals of not more than about 30 minutes per sample.

In preferred approaches for this embodiment, the first-dimension injection-to-injection interval is preferably not more than about 15 minutes, more preferably not more than about 10 minutes, and most preferably not more than about 8 minutes per sample. In some embodiments, the overall throughput of the two-dimensional chromatography system, as characterized by first-dimension injection-to-injection interval, can be not more than about 4 minutes, not more than about 2 minutes, not more than about 1 minute and/or not more than about 30 seconds per sample.

The number of sampled volumes for second-dimension analysis, the volume thereof, and the second-dimension sampling frequency can be the same as described above in connection with the regularly-recurring second-dimension injection interval embodiment. Additionally, coupled sampling between the first-dimension and second-dimension subsystems can be effected, as described above, such that a portion of the first-dimension separated components are sampled for injection into the second-dimension mobile phases at regularly recurring time intervals. In an alternative approach, however, the coupling can also be a controlled coupling. Specifically, a portion of the first-dimension separated components can be sampled for injection into the second-dimension mobile phases at intervals triggered by a control signal based on detection of the first-dimension separated components in the first-dimension mobile phase eluent. Moreover, the second dimension can have a single analysis channel, or can comprise parallel analysis channels, as described above.

Further details of this high-throughput embodiment are described as set forth in the Co-Owned Rapid Characterization of Polymers Application.

General Features and Protocols

The following features and protocols are general to each of the aforementioned embodiments, and can be applied generally thereto, and used in combination generally therewith.

Generally, the polymer samples being characterized can be non-biological polymers (e.g., non-biological copolymers) or biological polymers (e.g., proteins, DNA), and in many applications, are preferably non-biological polymers. In preferred embodiments, the polymer samples are libraries of polymer samples, such as spatially separated libraries of polymer samples—for example, as a microtiter plate for analysis in an analytical laboratory, or alternatively, such as temporally separated samples such as a series in time of on-line, near real time samples from an polymerization process line—for example, as part of a process monitoring and/or process control system. The libraries of polymer samples can be provided on a common substrate. The libraries of polymer samples can be synthesized in parallel using, for example, a parallel polymerization reactor. The libraries of polymer samples can comprise polymer samples that are polymerization product mixtures resulting from parallel polymerization reactions that are varied with respect to a factor affecting polymerization, such as one or more of reactant materials, catalysts, catalysts precursors, initiators, additives or the relative amounts thereof, or such as polymerization reaction conditions. The libraries of polymer samples can comprise polymer samples that are untreated, or pretreated only with one or more steps selected from the group consisting of non-chromatographic separation, dilution, mixing and redissolution. Further detailed description about the nature of the polymer samples, and/or of libraries of polymer samples, are included in the Co-Owned Rapid Characterization of Polymers Application, a portion of which is reproduced as follows:

Polymer Samples

The present invention is particularly preferred in connection with the characterization of polymer samples, and especially, combinatorial libraries comprising different polymer samples. The polymer sample can be a homogeneous polymer sample or a heterogeneous polymer sample, and in either case, comprises one or more polymer components. As used herein, the term "polymer component" refers to a sample component that includes one or more polymer molecules. The polymer molecules in a particular polymer component have the same repeat unit, and can be structurally identical to each other or structurally different from each other. For example, a polymer component may comprise a number of different molecules, with each molecule having the same repeat unit, but with a number of molecules having different molecular weights from each other (e.g., due to a different degree of polymerization). As another example, a heterogeneous mixture of copolymer molecules may, in some cases, be included within a single polymer component (e.g., a copolymer with a regularly-occurring repeat unit), or may, in other cases, define two or more different polymer components (e.g., a copolymer with irregularly-occurring or randomly-occurring repeat units). Hence, different polymer components include polymer molecules having different repeat units. It is possible that a particular polymer sample (e.g., a member of a library) will not contain a particular polymer molecule or polymer component of interest.

The polymer molecule of the polymer component is preferably a non-biological polymer. A non-biological polymer is, for purposes herein, a polymer other than an amino-acid polymer (e.g., protein) or a nucleic acid polymer (e.g., deoxyribonucleic acid (DNA)). The non-biological polymer molecule of the polymer component is, however, not generally critical; that is, the systems and methods disclosed herein will have broad application with respect to the type (e.g., architecture, composition, synthesis method or mechanism) and/or nature (e.g., physical state, form, attributes) of the non-biological polymer. Hence, the polymer molecule can be, with respect to homopolymer or copolymer architecture, a linear polymer, a branched polymer (e.g., short-chain branched, long-chained branched, hyper-branched), a cross-linked polymer, a cyclic polymer or a dendritic polymer. A copolymer molecule can be a random copolymer molecule, a block copolymer molecule (e.g., di-block, tri-block, multi-block, taper-block), a graft copolymer molecule or a comb copolymer molecule. The particular composition of the non-biological polymer molecule is not critical, and can include repeat units or random occurrences of one or more of the following, without limitation: polyethylene, polypropylene, polystyrene, polyolefin, polyimide, polyisobutylene, polyacrylonitrile, poly(vinyl chloride), poly(methyl methacrylate), poly(vinyl acetate), poly(vinylidene chloride), polytetrafluoroethylene, polyisoprene, polyacrylamide, polyacrylic acid, polyacrylate, poly(ethylene oxide), poly(ethyleneimine), polyamide, polyester, polyurethane, polysiloxane, polyether, polyphosphazine, polymethacrylate, and polyacetals. Polysaccharides are also preferably included within the scope of non-biological polymers. While some polysaccharides are of biological significance, many polysaccharides, and particularly semi-synthetic polysaccharides have substantial industrial utility with little, if any biological significance. Exemplary naturally-occurring polysaccharides include cellulose, dextran, gums (e.g., guar gum, locust bean gum, tamarind xyloglucan, pullulan), and other naturally-occurring biomass. Exemplary semi-synthetic polysaccharides having industrial applications include cellulose diacetate, cellulose triacetate, acylated cellulose, carboxymethyl cellulose and hydroxypropyl cellulose. In any case, such naturally-occurring and semi-synthetic polysaccharides can be modified by reactions such as hydrolysis, esterification, alkylation, or by other reactions.

In typical applications, a polymer sample is a heterogeneous sample comprising one or more polymer components, one or more monomer components and/or a continuous fluid phase. In copolymer applications, the polymer sample can comprise one or more copolymers, a first comonomer, a second comonomer, additional comonomers, and/or a continuous fluid phase. The polymer samples can, in any case, also include other components, such as catalysts, catalyst precursors (e.g., ligands, metal-precursors), solvents, initiators, additives, products of undesired side-reactions (e.g., polymer gel, or undesired homopolymer or copolymers) and/or impurities. Typical additives include, for example, surfactants, control agents, plasticizers, cosolvents and/or accelerators, among others. The various components of the heterogeneous polymer sample can be uniformly or non-uniformly dispersed in the continuous fluid phase.

The polymer sample is preferably a liquid polymer sample, such as a polymer solution, a polymer emulsion, a polymer dispersion or a polymer that is liquid in the pure state (i.e., a neat polymer). A polymer solution comprises one or more polymer components dissolved in a solvent. The polymer solution can be of a, form that includes well-dissolved chains and/or dissolved aggregated micelles. The solvent can vary, depending on the application, for example with respect to polarity, volatility, stability, and/or inertness or reactivity. Typical solvents include, for example, tetrahydro furan (THF), toluene, hexane, ethers, trichlorobenzene, dichlorobenzene, dimethylformamide, water, aqueous buffers, alcohols, etc. According to traditional chemistry conventions, a polymer emulsion can be considered to comprise one or more liquid-phase polymer components emulsified (uniformly or non-uniformly) in a liquid continuous phase, and a polymer dispersion can be considered to comprise solid particles of one or more polymer components dispersed (uniformly or non-uniformly) in a liquid continuous phase. The polymer emulsion and the polymer dispersion can also be considered, however, to have the more typically employed meanings specific to the art of polymer science—of being a emulsion-polymerization product and dispersion-polymerization product, respectively. In such cases, for example, the emulsion polymer sample can more generally include one or more polymer components that are insoluble, but uniformly dispersed, in a continuous phase, with typical emulsions including polymer component particles ranging in diameter from about 2 nm to about 500 nm, more typically from about 20 nm to about 400 nm, and even more typically from about 40 nm to about 200 nm. The dispersion polymer sample can, in such cases, generally include polymer component particles that are dispersed (uniformly or nonuniformly) in a continuous phase, with typical particles having a diameter ranging from about 0.2 $\mu$m to about 1000 $\mu$m, more typically from about 0.4 $\mu$m to about 500 $\mu$m, and even more typically from about 0.5 $\mu$m to about 200 $\mu$m. Exemplary polymers that can be in the form of neat polymer samples include dendrimers, and siloxane, among others. The liquid polymer sample can also be employed in the form of a slurry, a latex, a microgel a physical gel, or in any other form sufficiently tractable for analysis as described and claimed herein. Liquid samples are useful in the automated sample-handling tools that prepare and automatically sample each member of a polymer library. Liquid samples also allow the sample to flow in the chromatographic system or characterization system. In some cases, polymer synthesis reactions (i.e., polymerizations) directly produce liquid samples. These may be bulk liquid polymers, polymer solutions, or heterogeneous liquid samples such as polymer emulsions, lattices, or dispersions. In other cases, the polymer may be synthesized, stored or otherwise available for characterization in a non-liquid physical state, such as a solid state (e.g., crystalline, semi-crystalline or amorphous), a glassy state or rubbery state. Hence, the polymer sample may need to be dissolved, dispersed or emulsified to form a liquid sample by addition of a continuous liquid-phase such as a solvent. The polymer sample can, regardless of its particular form, have various attributes, including variations with respect to polarity, solubility and/or miscibility.

In preferred applications, the polymer sample is a polymerization product mixture. As used herein; the term "polymerization product mixture" refers to a mixture of sample components obtained as a product from a polymerization reaction. An exemplary polymerization product mixture can be a sample from a combinatorial library prepared by polymerization reactions, or can be a polymer sample drawn off of an industrial process line. In general, the polymer sample may be obtained after the synthesis reaction is stopped or completed or during the course of the polymerization reaction. Alternatively, samples of each polymerization reaction can be taken and placed into an intermediate array of vessels at various times during the course of the synthesis, optionally with addition of more solvent or other reagents to arrest the synthesis reaction or prepare the samples for analysis. These intermediate arrays can then be characterized at any time without interrupting the synthesis reaction. It is also possible to use polymer samples or libraries of polymer samples that were prepared previously and stored. Typically, polymer libraries can be stored with agents to ensure polymer integrity. Such storage agents include, for example, antioxidants or other agents effective for preventing cross-linking of polymer molecules during storage. Depending upon the polymerization reaction, other processing steps may also be desired, all of which are preferably automated. The polymerization scheme and/or mechanism by which the polymer molecules of the polymer component of the sample are prepared is not critical, and can include, for example, reactions considered to be addition polymerization, condensation polymerization, step-growth polymerization, and/or chain-growth polymerization reactions. Viewed from another aspect, the polymerization reaction can be an emulsion polymerization or a dispersion polymerization reaction. Viewed more specifically with respect to the mechanism, the polymerization reaction can be radical polymerization, ionic polymerization (e.g., cationic polymerization, anionic polymerization), and/or ring-opening polymerization reactions, among others. Non-limiting examples of the foregoing include, Ziegler-Natta or Kaminsky-Sinn reactions and various copolymerization reactions. Polymerization product mixtures can also be prepared by modification of a polymeric starting materials, by grafting reactions, chain extension, chain scission, functional group interconversion, or other reactions.

The sample size is not narrowly critical, and can generally vary, depending on the particular characterization protocols and systems used to characterize the sample or components thereof. Typical sample sizes can range from about 0.1 $\mu$l to about 1 $\mu$l, more typically from about 1 $\mu$l to about 1000 $\mu$l, even more typically from about 5 $\mu$l to about 100 $\mu$l, and still more typically from about 10 $\mu$l to about 50 $\mu$l. A generally preferred sample size for flow characterization systems and, particularly for liquid chromatography, is a sample size of about 20 $\mu$l.

The polymer sample, such as a polymerization product mixture, can be a raw, untreated polymer sample or can be pretreated in preparation for characterization. Typical sample preparation steps include preliminary, non-chromatographic separation of one or more components of a polymer sample from other components, dilution, mixing and/or redissolution (e.g., from a solid state), among other operations. Preliminary separation methods can help remove large-scale impurities such as dust, coagulum or other impurities. Such separation methods can include, for example: filtering (e.g., with a microfilter having pore sizes that allow the passage of particles less than about 0.5 $\mu$m or 0.2 $\mu$m); precipitation of polymer components, monomer components and/or other small-molecule components, decanting, washing, scavenging (e.g., with drying agents), membrane separation (e.g., diafiltration, dialysis), evaporation of volatile components and/or ion-exchange. The sample is preferably diluted, if necessary, to a concentration range suitable for detection. For typical liquid chromatography applications, for example, the sample concentration prior to loading into the liquid chromatography system can range from about 0.01 mg/ml to a neat sample, more typically from about 0.01 mg/ml to about 100 mg/ml, and even more typically from about 0.1 mg/ml to about 50 mg/ml. More specific concentration ranges typical for liquid chromatography samples include from about 0.1 mg/ml to about 20 mg/ml, and from about 0.5 mg/ml to about 5 mg/ml. For flow-injection analysis systems, in which the sample is detected without substantial chromatographic separation thereof, much more dilute solutions can be employed. Hence, the concentration can range from a detectable concentration level (for the particular detector employed) up to about 1 mg/ml, or more in some applications. Typical concentrations can be about $1\times10^{-2}$ wt %, about $1\times10^{-3}$ wt % or about $1\times10^{-4}$ wt %. Mixing can be required to increase the uniformity of a polymer sample emulsion or dispersion, and/or to integrate one or more additional components into the polymer sample. Preparation steps, and particularly rapid preparation techniques, can be an important aspect for combinatorial polymer investigations—since polymer samples may be synthesized in a form not ideally suited for immediate characterization.

Although the primary applications of the present invention are directed to combinatorial polymer science research and/or quality control for industrial polymer synthesis or processing protocols, aspects of the invention can have applications involving non-polymer samples. A non-polymer sample can be a material that comprises an organic or an inorganic non-polymer element or compound. Oligomers are considered to be polymers rather than non-polymers. The non-polymer molecule is, in some cases, preferably a non-biological non-polymer element or compound. Such non-biological non-polymer elements or compounds include non-polymer elements or compounds other than those having a well-characterized biological activity and/or a primary commercial application for a biological field (e.g., steroids, hormones, etc.). More particularly, such non-biological, non-polymer elements or compounds can include organic or inorganic materials such as pigments, carbon powders (e.g., carbon black), metals, metal oxides, metal salts, metal colloids, metal ligands, etc, without particular limitation.

Pluralities of Samples/Libraries of Samples

A plurality of samples such as polymer samples comprises 2 or more samples that are physically or temporally separated from each other—for example, by residing in different sample containers, by having a membrane or other partitioning material positioned between samples, by being partitioned (e.g., in-line) with an intervening fluid, by being temporally separated in a flow process line (e.g., as sampled for process control purposes), or otherwise. The plurality of samples preferably comprises 4 or more samples, more preferably 8 or more samples, and even more preferably 10 or more samples. Four samples can be employed, for example, in connection with experiments having one control sample and three polymer samples varying (e.g., with respect to composition or process conditions as discussed above) to be representative of a high, a medium and a low-value of the varied factor—and thereby, to provide some indication as to trends. Eight samples can provide for additional variations in the explored factor space. Moreover, eight samples corresponds to the number of parallel polymerization reactors in the PPR-8™, being selectively offered as one of the Discovery Tools™ of Symyx Technologies, Inc. (Santa Clara, Calif.). Higher numbers of samples can be investigated, according to the methods of the invention, to provide additional insights into larger compositional and/or process space. In some cases, for example, the plurality of samples can be 15 or more samples, preferably 20 or more samples, more preferably 40 or more samples and even more preferably 80 or more samples. Such numbers can be loosely associated with standard configurations of parallel reactor configurations (e.g., the PPR-48™, Symyx Technologies, Inc.) and/or of standard sample containers (e.g., 96-well microtiter plate-type formats). Moreover, even larger numbers of samples such as polymer samples can be characterized according to the methods of the present invention for larger scale research endeavors. Hence, the number of samples can be 150 or more, 400 or more, 500 or more, 750 or more, 1,000 or more, 1,500 or more, 2,000 or more, 5,000 or more and 10,000 or more polymer samples. As such, the number of samples can range from about 2 samples to about 10,000 samples, and preferably from about 8 samples to about 10,000 samples. In many applications, however, the number of samples can range from about 80 samples to about 1500 samples. In some cases, in which processing of samples using typical 96-well microtiter-plate formatting is convenient or otherwise desirable, the number of samples can be 96*N, where N is an integer ranging from about 1 to about 100. For many applications, N can suitably range from 1 to about 20, and in some cases, from 1 to about 5.

The plurality of samples can be a combinatorial library of samples. A library of samples comprises two or more different samples, and can be in an array format as spatially separated samples—preferably on a common substrate, or temporally separated—for example, in a flow system. Candidate samples (i.e., members) within a library may differ in a definable and typically predefined way, including with regard to chemical structure, processing (e.g., synthesis)

history, mixtures of interacting components, purity, etc. The samples can be spatially separated, preferably at an exposed surface of the substrate, such that the array of samples are separately addressable for sampling into the characterization system and subsequent characterization thereof. The two or more different samples can reside in sample containers formed as wells in a surface of the substrate. The number of samples included within the library can generally be the same as the number of samples included within the plurality of samples, as discussed above. In general, however, not all of the samples within a library of samples need to be different samples. When process conditions are to be evaluated, the libraries may contain only one type of sample. Typically, however, for combinatorial polymer science research applications, at least two or more, preferably at least four or more, even more preferably eight or more and, in many cases most, and allowably each of the plurality of polymer samples in a given library of polymer samples will be different from each other. Specifically, a different polymer sample can be included within at least about 50%, preferably at least 75%, preferably at least 80%, even more preferably at least 90%, still more preferably at least 95%, yet more preferably at least 98% and most preferably at least 99% of the polymer samples included in the sample library. In some cases, all of the polymer samples in a library of polymer samples will be different from each other.

The substrate can be a structure having a rigid or semi-rigid surface on which or into which the array of polymer samples can be formed or deposited. The substrate can be of any suitable material, and preferably consists essentially of materials that are inert with respect to the polymer samples of interest. Certain materials will, therefore, be less desirably employed as a substrate material for certain polymerization reaction process conditions (e.g., high temperatures—especially temperatures greater than about 100 C—or high pressures) and/or for certain reaction mechanisms. Stainless steel, silicon, including polycrystalline silicon, single-crystal silicon, sputtered silicon, and silica ($SiO_2$) in any of its forms (quartz, glass, etc.) are preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material in some applications. Organic and inorganic polymers may also be suitably employed in some applications of the invention. Exemplary polymeric materials that can be suitable as a substrate material in particular applications include polyimides such as Kapton™, polypropylene, polytetrafluoroethylene (PTFE) and/or polyether etherketone (PEEK), among others. The substrate material is also preferably selected for suitability in connection with known fabrication techniques. As to form, the sample containers formed in, at or on a substrate can be preferably, but are not necessarily, arranged in a substantially flat, substantially planar surface of the substrate. The sample containers can be formed in a surface of the substrate as dimples, wells, raised regions, trenches, or the like. Non-conventional substrate-based sample containers, such as relatively flat surfaces having surface-modified regions (e.g., selectively wettable regions) can also be employed. The overall size and/or shape of the substrate is not limiting to the invention. The size and shape can be chosen, however, to be compatible with commercial availability, existing fabrication techniques, and/or with known or later-developed automation techniques, including automated sampling and automated substrate-handling devices. The substrate is also preferably sized to be portable by humans. The substrate can be thermally insulated, particularly for high-temperature and/or low-temperature applications. In preferred embodiments, the substrate is designed such that the individually addressable regions of the substrate can act as polymerization reaction vessels for preparing a polymerization product mixture (as well as sample containers for the two or more different polymer samples during subsequent characterization thereof. Glass-lined, 96-well, 384-well and 1536-well microtiter-type plates, fabricated from stainless steel and/or aluminum, are preferred substrates for a library of polymer samples. The choice of an appropriate specific substrate material and/or form for certain applications will be apparent to those of skill in the art in view of the guidance provided herein.

The library of polymer materials can be a combinatorial library of reaction product mixtures such as polymerization product mixtures. Polymer libraries can comprise, for example, polymerization product mixtures resulting from polymerization reactions that are varied with respect to, for example, reactant materials (e.g., monomers, comonomers), catalysts, catalyst precursors, initiators, additives, the relative amounts of such components, reaction conditions (e.g., temperature, pressure, reaction time) or any other factor affecting polymerization. Design variables for polymerization reactions are well known in the art. See generally, Odian, *Principles of Polymerization*, $3^{rd}$ Ed., John Wiley & Sons, Inc. (1991). A library of polymer samples may be prepared in arrays, in parallel polymerization reactors or in a serial fashion. Exemplary methods and apparatus for preparing polymer libraries—based on combinatorial polymer synthesis approaches—are disclosed in copending U.S. patent application Ser. No. 09/211,982 of Turner et al. filed Dec. 14, 1998, copending U.S. patent application Ser. No. 09/227,558 of Turner et al. filed Jan. 8, 1999, copending U.S. patent application Ser. No. 09/235,368 of Weinberg et al. filed Jan. 21, 1999, and copending U.S. provisional patent application Ser. No. 60/122,704 entitled "Controlled, Stable Free Radical Emulsion and Water-Based Polymerizations", filed Mar. 9, 1999 by Klaerner et al. See also, PCT Patent Application WO 96/11878.

The libraries can be advantageously characterized directly, without being isolated, from the reaction vessel in which the polymer was synthesized. Thus, reagents, catalysts or initiators and other additives for making polymers may be included with the polymer sample for characterization or screening.

While such methods are preferred for a combinatorial approach to polymer science research, they are to be considered exemplary and non-limiting. As noted above, the particular polymer samples characterized according to the methods and with the apparatus disclosed herein can be from any source, including, but not limited to polymerization product mixtures resulting from combinatorially synthesis approaches.

Mini- and Micro-Scale Applications

The methods of the present invention can be applied in connection with "normal" scale HPLC systems, and can also be applied to smaller scale systems—including particularly mini-scale systems and micro-scale systems. As used herein, mini-scale systems are considered to include those having mobile-phase supply conduits and/or separation units (e.g., chromatographic columns) with a diameter ranging from about 3 mm to about 500 $\mu$m, and micro-scale systems are considered to include those having mobile-phase supply conduits with a diameter of about 500 $\mu$m or less. For other than circular cross-sections, equivalent dimensions can be determined based on hydraulic radius.

Preferably at least one of the first or second dimensions are high-performance liquid chromatography subsystems adapted for gel permeation chromatography. In a particularly preferred approach, the first dimension HPLC subsystem can be adapted for chromatographic approaches effective for distinguishing between chemical composition and/or structural variations of polymer sample components (e.g., repeat units types, ratios of copolymer repeat units, functional groups, branching, etc.). Exemplary preferred first-dimension HPLC subsystems include reverse phase chromatography subsystems, mobile-phase compositional gradient elution chromatography subsystems (e.g., compositionally-varying mobile phase gradients and/or temperature-varying mobile phase gradients), or mobile-phase temperature gradient elution chromatography subsystems. Mobile-phase elution gradients of the first dimension preferably comprise a substantially universal co-solvent system, such as a water-tetrahydrofuran-hexane system. Generally, in this particularly preferred approach, the second dimension HPLC subsystem is preferably adapted for size-exclusion chromatography (SEC) such as gel permeation chromatography (GPC).

The methods can further comprise determining a property of interest from the detected property of the first-dimension and/or second dimension. The detector type is not generally critical, and can include for example, mass detectors and/or concentration detectors. Evaporative light scattering detectors (ELSD) are preferred in some embodiments. Further details about detection, including types of detectors and various combinations of detectors, and including various types of detected and/or determined properties, is described in detail in the attached Co-Owned Rapid Characterization of Polymers Application.

The multi-dimensional HPLC system of the invention is preferably operated under the control of one or more microprocessors (not shown), preferably configured with software effective for operating the hardware (sampling systems, injection valves, mobile-phase pumps, detection systems) and for effecting tracking and acquiring data, etc. Such suitable software is commercially available, for example, from liquid chromatography systems manufacturers, such as Millenium software (Waters), and/or from software manufacturers, such as Lab View brand software. The software can, if necessary, be modified to incorporate functionality for driving the aforementioned hardware and data tracking and acquisition needs for the first and second dimension HPLC subsystems. In a preferred embodiment, for example, with reference to FIG. 1, Lab View software can be modified to (i) integrate with Impressionist™ robotic-control software (Symyx Technologies, Inc., Santa Clara, Calif.) used for controlling the robotic pipette (Cavro Instruments, Inc.) hardware for serially withdrawing polymer samples 100 from a library of polymer samples, and for injecting such polymer samples into a loading port 1310 of a first-dimension injector 1300, such integration including tracking of timing of injection as an initiation point for the two-dimensional chromatography analysis methodologies programmed into the Lab View software; (ii) to control first-dimension HPLC analysis operations, including first-dimension mobile phase pumps 1200 to control first-dimension mobile phase flow rates, and if desired, temperature control of the mobile phase and/or column, and if desired, first-dimension mobile phase source selection valves (not shown) for providing mobile phase gradients for first-dimension gradient elution chromatography; (iii) to control second-dimension HPLC analysis operations, including the second-dimension injector 2300 for comprehensive, directly coupled sampling from the first dimension to the second dimension (e.g., such as regularly recurring interval sampling), the mobile phase pumps 2200 to control second-dimension mobile phase flow rates, and if desired, temperature control of the mobile phase and/or column, and if desired, second-dimension mobile phase source selection valves (not shown) for providing mobile phase gradients for first-dimension gradient elution chromatography, the second-dimension detector(s) 2600 for data acquisition and handling, etc.

Figures 3A, 3B:
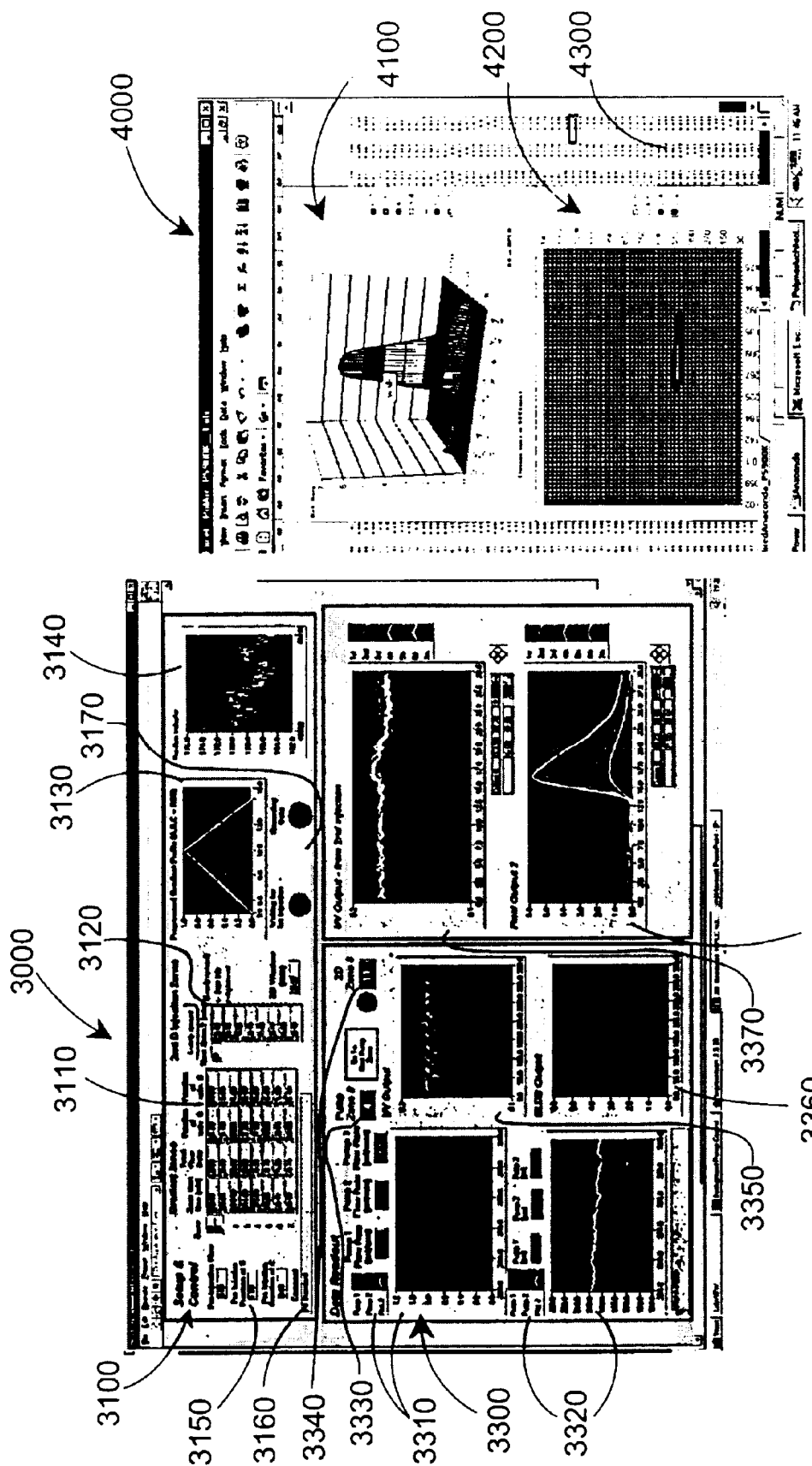
FIGS. 3A and 3B are screen shots of graphical user interfaces that allow for efficient user-driven control of hardware and data management functions of a two-dimensional liquid chromatography system, as well as for integrated display (FIG. 3A) or separate display (FIG. 3B) of resulting characterization data.

As shown in FIGS. 3A and 3B, for example, the customized Lab View software can include a graphical user interface that allows for efficient user-driven control of such hardware and data management functions, as well as for integrated or separate display of resulting characterization data. Briefly, FIG. 3A shows a graphical user interface computer screen shot 3000 that includes a set-up and control panel 3100 and a data readout panel 3300. The set-up and control panel 3100 comprises several subpanels or sections, including a gradient zones selection section 3110, a 2-D injection zone selection section 3120, a programmed gradient profile display section 3130, a pre-flow indicator display section 3140, a pre-injection selection section 3150, a comment section 3160, and an indicator section 3170. The pre-injection selection section 3150 comprises data entry boxes for selecting pre-injection flow rates, pre-injection fraction of one of the mobile-phase sources, and pre-injection fraction of another of the mobile-phase sources. The gradient zone selection section 3110 includes drop-down data entry boxes for selecting gradient zones, zone start times, total flow rates, fraction of one solvent of the mobile-phase gradient, and fraction of another solvent of the mobile phase gradient. The 2-D injection zone selection section 3120 comprises drop-down data entry boxes for defining the time of the gradient zones, a selection tab for optionally selecting evenly spaced gradient zones, and a drop-down data entry box for defining the duration of the second-dimension analysis. The programmed gradient profile display section 3130 comprises a graphical display area for showing the programmed gradient profile for each of the mobile-phase sources (e.g., solvents). The pre-flow indicator display section 3140 comprises a graphical display area for graphically displaying the pre-injection flow rate over time. The comment section 3160 includes a data entry box for entering comments. The indicator section 3170 includes a red indicator light for indicating waiting for first injection, and a second green indicator light for indicating that the system is recording data. The data readout panel 3300 also comprises several subpanels or sections, including a pump flow rate indication and display section 3310, a pump-pressure indication and display section 3320, a pump zone indication section 3330, a 2-D zone indication section 3340, a UV detector output display section 3350, an ELSD output display section 3360, a UV output from $2^{nd}$ injection display section 3370, and a final output display section 3380. The pump flow rate indication and display section 3310 comprises indicator boxes and a display panel for pump flow rates, together with a display panel for a legend of the display panel, the pump-pressure indication and display section 3320 comprises indicator boxes and a display panel for pump pressure, together with a display panel for a legend of the display panel, the pump zone indication section 3330 comprises an indicator box for pump zones, the 2-D zone indication section 3340 comprises an indicator box for 2-dimensional zone, the UV detector output display section 3350 comprises a display box for the UV detector data, the ELSD output display section 3360 comprises a display box for the ELSD detector data, the UV output from $2^{nd}$ injection display section 3370 comprises a display box for all of the $2^{nd}$ injection UV detector data, together with a display panel for the legend thereof, and a final output display section 3380 comprising a display box for the final output data, together with a display panel for a legend thereof. FIG. 3B shows a graphical user interface computer screen shot 4000 that includes a 3-dimensional graphical display panel 4100 and a two-dimensional graphical display panel 4200, as well as a raw data display panel 4300. The 3-dimensional graphical display panel 4100 comprises a three-dimensional representation of the detector response versus first-dimension retention time and versus second-dimension retention time, together with a legend display panel. The two-dimensional graphical display panel 4200 comprises a two-dimensional contour plot of first-dimension retention time versus second-dimension retention time, as well as a legend display panel. The raw data display panel 4300 comprises a table of raw data.

Further details about microprocessor control of the HPLC subsystems, is described in detail in the attached Co-Owned Rapid Characterization of Polymers Application and in the attached Co-Owned Parallel HPLC Application.

The following examples illustrate the principles and advantages of the invention.

EXAMPLES

Example 1
Two-Dimensional Liquid Chromatography with Regularly Recurring $2^{nd}$-Dimension Sampling Interval This example demonstrates two-dimensional liquid chromatography techniques for characterizing a polymer sample comprising polymer components of varying composition and/or molecular weight, wherein the second-dimension is comprehensively and directly coupled to the first dimension, by in-line sampling of the first-dimension mobile phase eluent at regularly recurring intervals of time.

In experiments effected for this example, various polymer samples (described below) having components with different chemical compositions and/or molecular weight were characterized in a two-dimension chromatography system comprising a first dimension HPLC subsystem adapted for normal-phase compositional gradient elution chromatography, and a second dimension HPLC subsystem adapted for gel permeation chromatography (GPC). Briefly, about 50 μL of a polymer sample solution was injected into the mobile phase of the first dimension, and chromatographically separated in a first-dimension HPLC column having separation media effective for normal-phase separation, using a relay hexane-tetrahydrofuran water gradient elution at a first-dimension flow rate of about 0.5 mL/min. The first-dimension mobile phase eluent coming of the first-dimension HPLC column was sampled using a multi-port injection valve configured with two sample loops, each having a volume of about 250 μl. Discrete volume fractions (250 μl) of the first-dimension mobile phase eluent were sampled at regularly recurring intervals with a frequency of about 30 seconds per sample, and the sampled portions were injected at the same time frequency into a second-dimension mobile phase. Chromatographic separation in the second-dimension was effected using a second-dimension column having separation media effective for size-exclusion chromatography (SEC), specifically, gel permeation chromatography (GPC), and using DMF as the mobile phase at a second-dimension flow rate of about 4 mL/min. Detection was effected by routing all of the eluent from the GPC column into an evaporative light scattering detector, the signal of which is proportional to the concentration of polymer in the second-dimension mobile phase eluent. A 2-dimensional (2-D) chromatogram or 2-D map was composed by stacking individual chromatograms corresponding to 30 second intervals that represent the SEC chromatographic traces. The first dimension retention time was represented by the time of sampling of a particular fraction from the first-dimension mobile phase eluent for injection into the second-dimension.

In a first experiment, the second-dimension SEC subsystem was calibrated by characterizing a set of polystyrene polymer standards combined as a single sample—as a single "shot" in the aforementioned two-dimensional liquid chromatography system. Hence, the polymer sample comprised a set of polystyrene polymer standards as polymer components having the same chemical composition, but different known molecular weights. The results, shown in FIGS. 4A and 4B, demonstrate that the second dimension provides adequate resolution of polymer sample components having different molecular weights in less than about 30 seconds. Specifically, FIG. 4A is a graph showing detector response (mV) versus retention time (min) with clear resolution of polystyrene standards subcomponents of different molecular weights. FIG. 4B is a graph showing the corresponding log molecular weigh data versus retention time (min) with the expected substantially linear relationship between components of the polystyrene standards sample. Hence, this first experiment demonstrates that adequate molecular weight resolution can be achieved in the second-dimension HPLC (SEC/GPC) subsystem with a regularly-recurring sampling interval from the first dimension, and injection to injection interval into the second dimension of about 30 seconds.

Figures 5A, 5B:
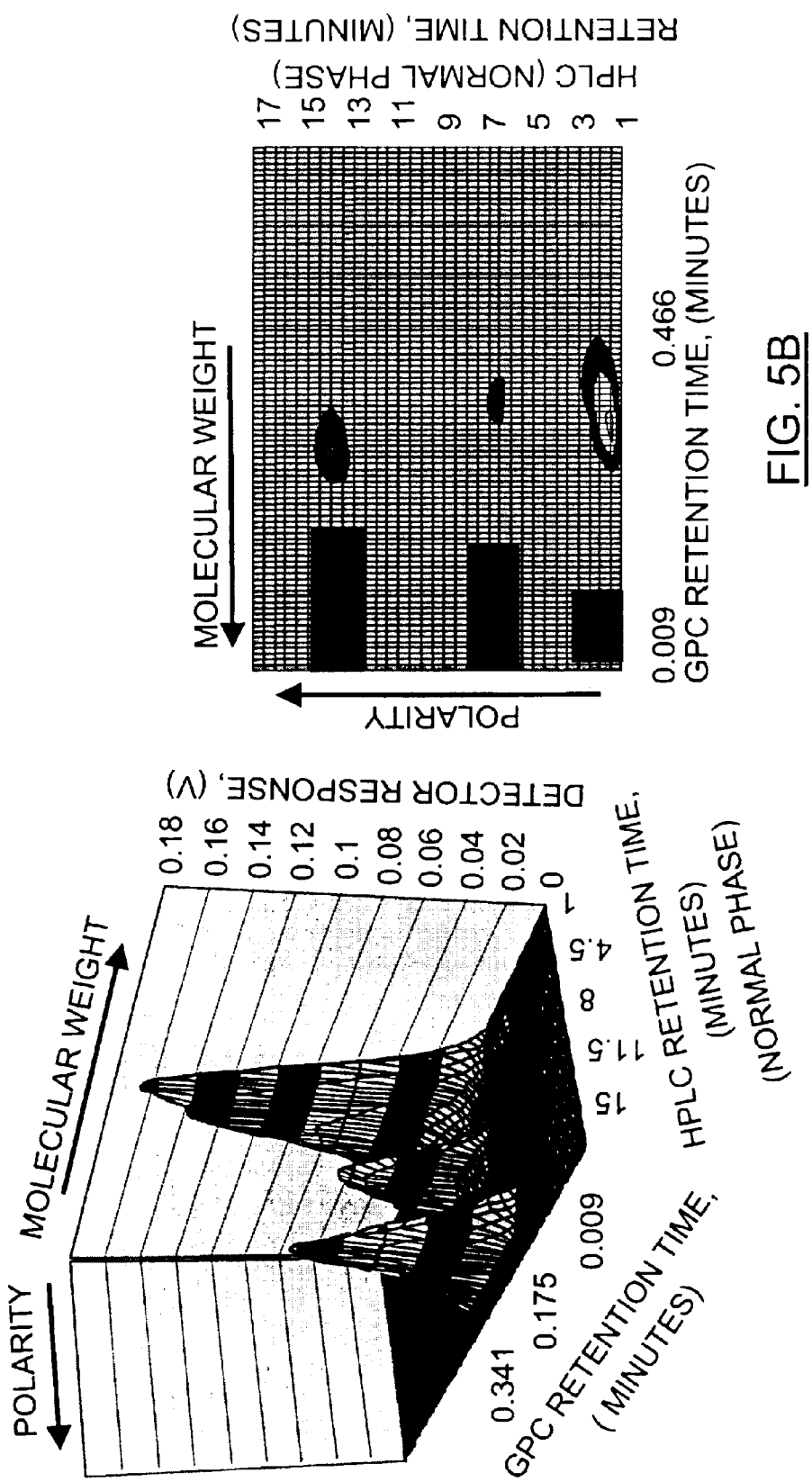
FIGS. 5A and 5B are graphical data showing the results of a multi-dimensional liquid chromatography experiment.

In a second experiment, a polymer solution comprising different types of polymers as sample polymer components was characterized to determine chemical composition distribution and molecular weight distribution in a single-shot sample analysis with a run time of about 15 minutes. Specifically, the polymer sample comprised polyhydroxyethylmethacrylate (PHEMA), polymethylmethacrylate (PMMA) and polystyrene (PS) components, each component having roughly the same molecular weight distribution. This polymer sample was characterized in the two-dimension chromatography system described above (normal phase HPLC first dimension/SEC (GPC) second dimension) using substantially the same operational protocols as described. The results, shown in FIGS. 5A and 5B, demonstrate that the first dimension provides adequate resolution of polymer sample components having different chemical compositions, but substantially the same molecular weight distribution under the aforementioned conditions and separation protocols, with about a 15 minute total run time (about 14½ minutes of which were for the first-dimension characterization, and about ½ minute of which was for the second dimension characterization). Specifically, FIG. 5A is a 3-dimensional plot showing detector response (V) versus both (i) normal-phase HPLC retention time (min), corresponding to the first-dimension separation, and (ii) GPC retention time (min), corresponding to the second-dimension separation, with clear resolution of the various types of polymer components in the polymer sample. FIG. 5B is a 2-dimensional contour graph showing the corresponding top-down view of the data presented in FIG. 5A, including normal-phase HPLC retention time (min), corresponding to the first-dimension separation versus GPC retention time (min), corresponding to the second-dimension separation, again showing clear resolution of the various types of polymer components in the polymer sample.

Figure 6:
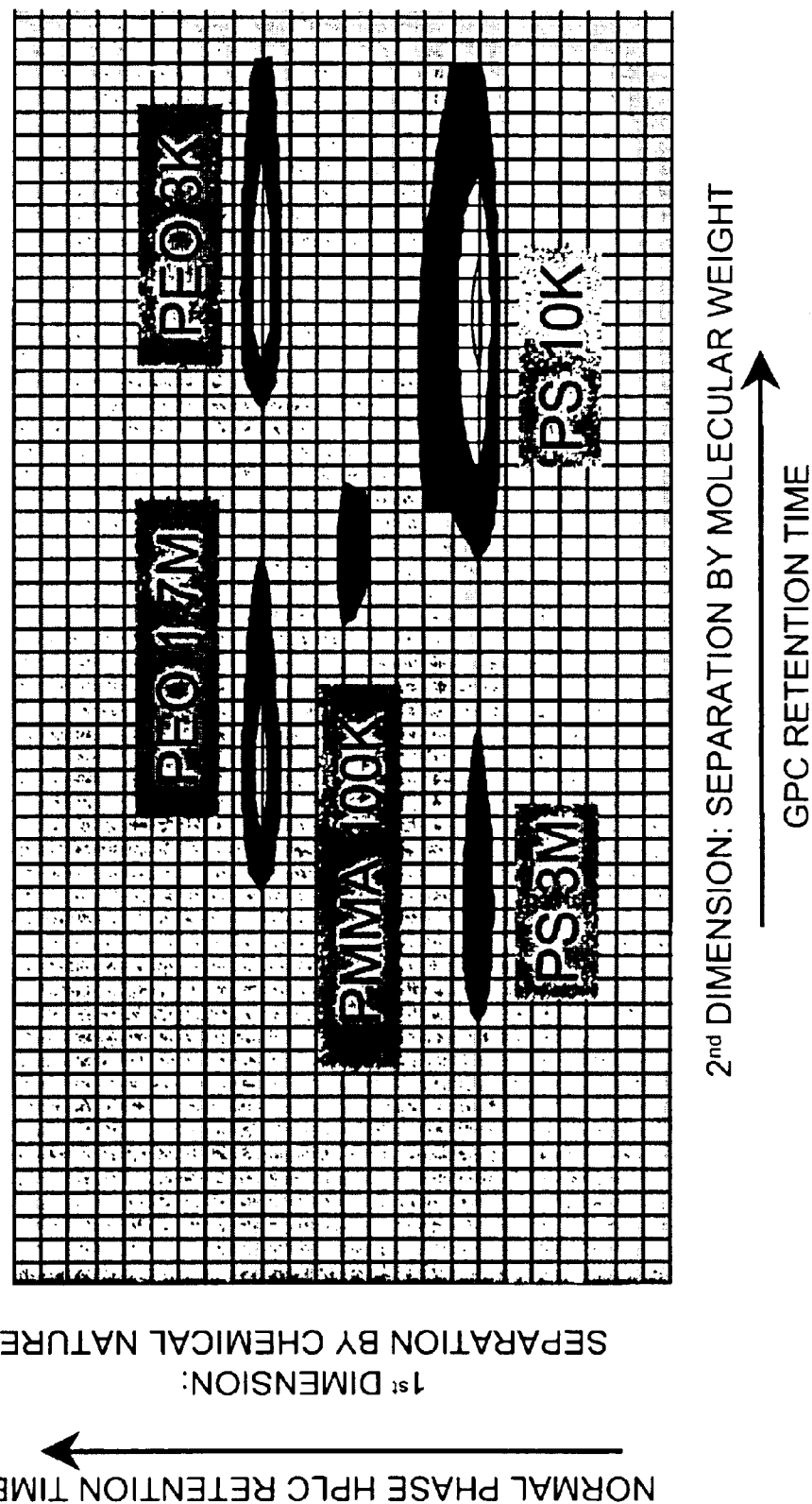
FIG. 6 is a 2-dimensional graph showing the results of a multi-dimensional liquid chromatography experiment, including specifically, the relative normal-phase HPLC retention time, corresponding to the first-dimension separation, versus the relative GPC retention time (min), corresponding to the second-dimension separation. Clear resolution of the various types of polymer components in the polymer sample is demonstrated.

In a third experiment, a polymer solution comprising sample components that included different types of polymers with different molecular weights, as well as the same types of polymers with different molecular weights, was characterized to determine chemical composition distribution and molecular weight distribution in a single-shot sample analysis. Specifically, the polymer sample comprised polymethylmethacrylate (PMMA, ~100 K molecular weight), polyethyleneoxide (PEO, ~1.7 M molecular weight), polyethyleneoxide (PEO, ~3 K molecular weight), polystyrene (PS, ~3 M molecular weight), and polystyrene (PS, ~10 K molecular weight) as components thereof. This polymer sample was characterized in the two-dimension chromatography system described above (normal phase HPLC first dimension/SEC (GPC) second dimension) using substantially the same operational protocols as described. The results, shown in FIG. 6, demonstrate that the two-dimensional liquid chromatography system provides adequate resolution of these polymer sample components—both with respect to chemical composition distribution and molecular weight distribution under the aforementioned conditions and separation protocols. Specifically, FIG. 6 is a 2-dimensional graph showing the relative normal-phase HPLC retention time, corresponding to the first-dimension separation, versus the relative GPC retention time (min), corresponding to the second-dimension separation. Clear resolution of the various types of polymer components in the polymer sample is demonstrated.

Example 2
Use of 2-Dimensional Liquid Chromatography for Fingerprinting Characterization of a Combinatorial Library of Polymer Samples This example demonstrates two-dimensional liquid chromatography techniques as applied for characterizing a combinatorial library of polymer samples comprising polymer components of random copolymers, poly(AB), synthesized by free-radical polymerization in a parallel batch reactor with various ratios of monomers A and B, and with varying ratios of monomer to initiator. This example also demonstrates that such two-dimensional characterization protocols are comparable in quality of results to separate, one-dimensional analysis conducted independently of each other, and favorable in terms of overall sample throughput.

Figure 7A:
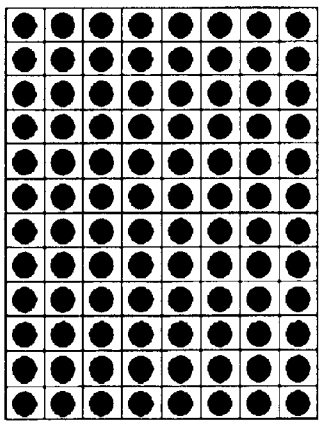
FIGS. 7A through 7C are graphical representations of the library design for a library of polymer samples (FIG. 7A), and the results of a multi-dimensional liquid chromatography experiment (FIGS. 7B and 7C). Specifically.

The polymer samples of the library were synthesized in the parallel batch reactor using combinatorial polymerization approaches known in the art. FIG. 7A is a graphical representation of the library design for the library of polymer samples, showing that (i) the relative ratio of monomer A to monomer B ranges from about 0 to about 1 along each of the rows of the synthesis reactor (microtiter-type format), and is about the same in each of the columns thereof, and that (ii) the relative ratio of monomer to initiator increases along each of the columns of the synthesis reactor (moving from top to bottom, as shown), and is about the same in each of the rows thereof.

Figure 7C:
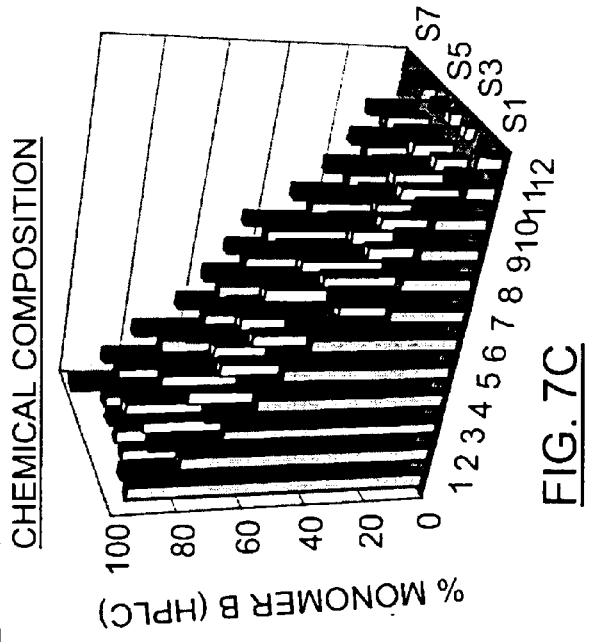
Figure 7B:
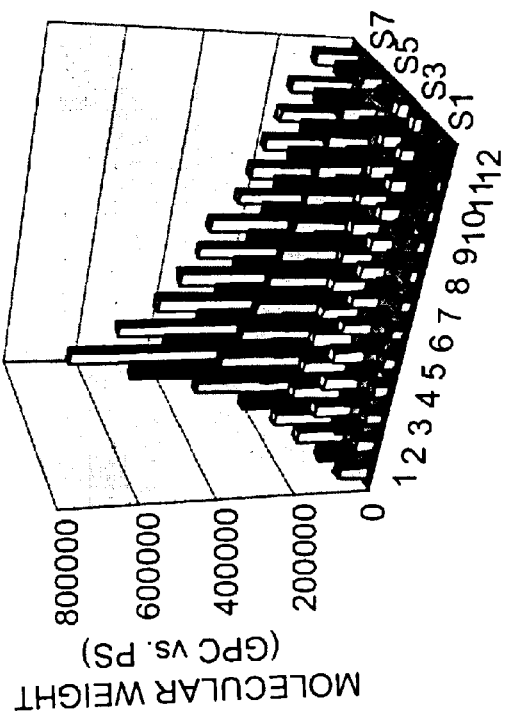

The polymer samples of the library were characterized in a comprehensive, directly-coupled two-dimension liquid chromatography system comprising a first dimension HPLC subsystem adapted for normal-phase compositional gradient elution chromatography, and a second dimension HPLC subsystem adapted for gel permeation chromatography (GPC). The operational conditions and protocols for the two-dimensional liquid chromatography system was substantially the same as that described in connection with Example 1. The results, shown in FIGS. 7B and 7C, demonstrate that the two-dimension HPLC system provides substantial resolution of polymer sample fingerprints—chemical composition and molecular weight data for each of the polymer samples of the library. Specifically, FIG. 7B is a 3-dimensional plot showing molecular weight, as determined from second-dimension GPC data versus polystyrene standard calibration, versus spatial position in the microtiter-format parallel reactor (columns 1–12 and rows 1–7). FIG. 7C is a 3-dimensional plot showing chemical composition, as determined from first-dimension normal phase HPLC data (and shown as % of monomer B incorporated into each of the random copolymer samples), versus spatial position in the microtiter-format parallel reactor (columns 1–12 and rows 1–7).

Example 3
Comparative Characterization Using 2-Dimensional Liquid Chromatography versus Using Separate, One-Dimension HPLC and GPC Analysis, for Fingerprinting Characterization of a Combinatorial Library of Polymer Samples This example demonstrates a comparison between two-dimensional liquid chromatography techniques, and corresponding separate, individual one-dimensional liquid chromatography protocols, as applied for characterizing a combinatorial library of polymer samples. The library of polymer samples comprises polymer components of random copolymers, poly(AB), synthesized by free-radical polymerization in a parallel batch reactor with various ratios of monomers A and B, and with varying ratios of monomer to initiator, where A and B represent hydroxyethylmethacrylate (HEMA) and styrene monomers, respectively.

The polymer samples of the library were synthesized in the parallel batch reactor using combinatorial polymerization approaches known in the art. FIG. 8A is a graphical representation of the library design for the library of polymer samples, showing that (i) the relative ratio of monomer A to monomer B ranges from about 0 to about 1 along each of the rows of the synthesis reactor (microtiter-type format), and is about the same in each of the columns thereof, and that (ii) the relative ratio of monomer to initiator increases along each of the columns of the synthesis reactor (moving from top to bottom, as shown), and is about the same in each of the rows thereof.

The polymer samples of the library were characterized in a comprehensive, directly-coupled two-dimension liquid chromatography system comprising a first dimension HPLC subsystem adapted for normal-phase compositional gradient elution chromatography, and a second dimension HPLC subsystem adapted for gel permeation chromatography (GPC). The operational conditions and protocols for the two-dimensional liquid chromatography system was substantially the same as that described in connection with Example 1. The results of the two-dimensional characterization are shown in FIG. 8B. FIG. 8B is an array of 2-dimensional contour graphs, each graph representing data from one of the samples of the library, and each graph showing chemical composition distribution (represented as normal phase HPLC retention time, corresponding to the relative amount of monomer B in each of the samples), versus molecular weight distribution (represented as GPC retention time (-log MW)). Note that for simplicity of presentation, the data included in FIG. 8B corresponds to only three rows of the polymer samples of the library of FIG. 8A.

For comparative purposes, the library of polymer samples (FIG. 8A) was characterized using two separate HPLC characterization techniques, as one-dimensional analysis independent of each other: normal phase HPLC gradient elution chromatography and rapid-analysis GPC chromatography, each of which was effected using conditions and protocols substantially the same as those used in the first-dimension subsystem and second-dimensions subsystem of the two-dimensional analysis (see Example 1). FIG. 8C shows the results of the independent, one-dimensional analysis for the same polymer samples for which data is shown in FIG. 8B. Specifically, FIG. 8C is an array of 2-dimensional plots, each plot representing the combined, independently-obtained data from one of the samples of the library, and each plot showing chemical composition (represented as the relative amount of monomer B in each of the samples as determined by the independent, one-dimension normal phase HPLC gradient elution characterization), versus molecular weight (represented as GPC log MW). Note that the molecular weight units in FIG. 8C are the opposite in sign from those of FIG. 8B, requiring an inversion of data for comparison purposes between FIGS. 8B and 8C.

Comparison of FIGS. 8B and 8C demonstrates that the two-dimensional characterization protocols are comparable or favorable to separate, one-dimensional analysis conducted independently of each other, with respect to quality of analysis results and the capability to identify trends and associate those trends with the polymerization synthesis conditions. Significantly, the data obtained from the two-dimensional characterization scheme allows for distribution data profiles, whereas the two separate, independent one-dimensional analysis allows for only overall molecular weight/chemical composition information. Additionally, the two-dimensional chromatography was favorable to the separate, one-dimensional analysis approach in terms of overall sample throughput.

Example 4
Comparative Characterization Using 2-Dimensional Liquid Chromatography Versus Using Traditional GPC-FTIR Analysis, for Polymer Sample Fingerprinting This example demonstrates a comparison between two-dimensional liquid chromatography techniques, and traditional gel permeation chromatography-Fourier transformed infrared (GPC-FTIR) analysis for fingerprinting of a polymer sample. The example shows, in particular, that two-dimensional liquid chromatography is a more definitive technique for distinguishing whether the polymer sample comprises a polymer blend of two different polymer types and/or molecular weights, or whether the polymer sample comprises a single copolymer. Moreover, the more definitive result of the two-dimensional analysis was obtained in about 15 minutes—about ⅛ of the overall characterization time using the traditional GPC-FTIR approach (about 2 hours).

The polymer comprised polymethylmethacrylate (PMMA) and polystyrene (PS) components, each component having roughly the same molecular weight distribution.

Figures 9A, 9B:
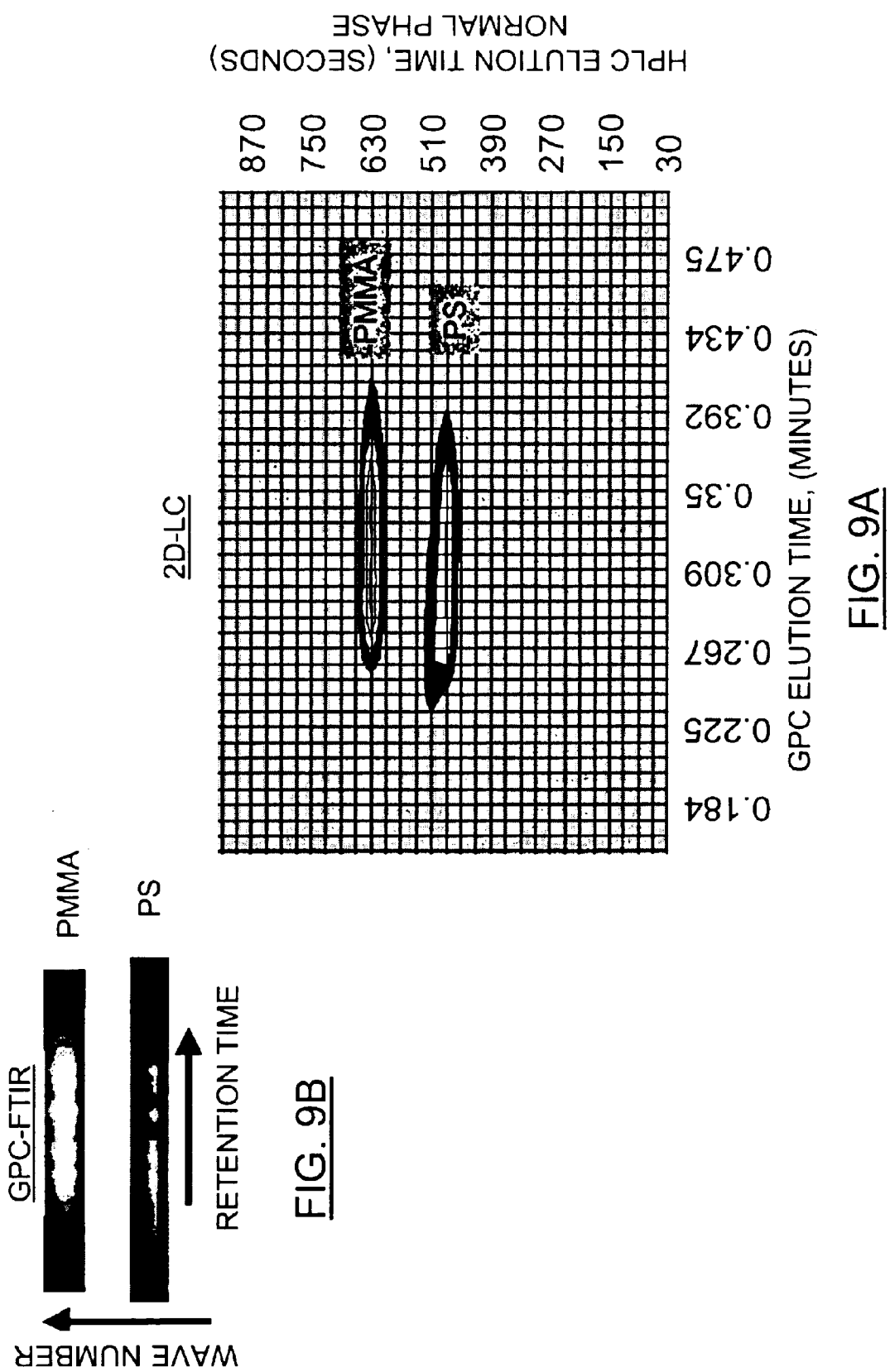
FIGS. 9A and 9B are plots showing data from a characterization of a polymer sample using two-dimensional chromatography (FIG. 9A) and using a conventional GPC-FTIR techniques (FIG. 9B).

This polymer sample was first characterized in the two-dimension chromatography system described in connection with Example 1 (normal phase HPLC first dimension/SEC (GPC) second dimension) using substantially the same operational protocols as described in Example 1, with a total sample analysis time of about 15 minutes. The results, shown in FIG. 9A, demonstrate that the two-dimensional characterization approach resolved the sample components into separate components, thereby allowing for positive identification of the polymer sample as a blend of the two polymer components. Specifically, FIG. 9A is a 2-dimensional contour graph showing normal-phase HPLC retention time (sec), corresponding to the first-dimension separation, versus GPC retention time (min), corresponding to the second-dimension separation, with clear resolution of the polymer components.

This sample was also characterized in a traditional GPC-FTIR analysis system, in which fractions from a GPC system were spotted onto an array, and subsequently analyzed using FTIR techniques. The total analysis time required about two hours. The results, shown in FIG. 9B, demonstrate that the analysis remains inconclusive as to whether the polymer sample was a copolymer or whether it comprised a blend of two polymer components.

Figure 10:
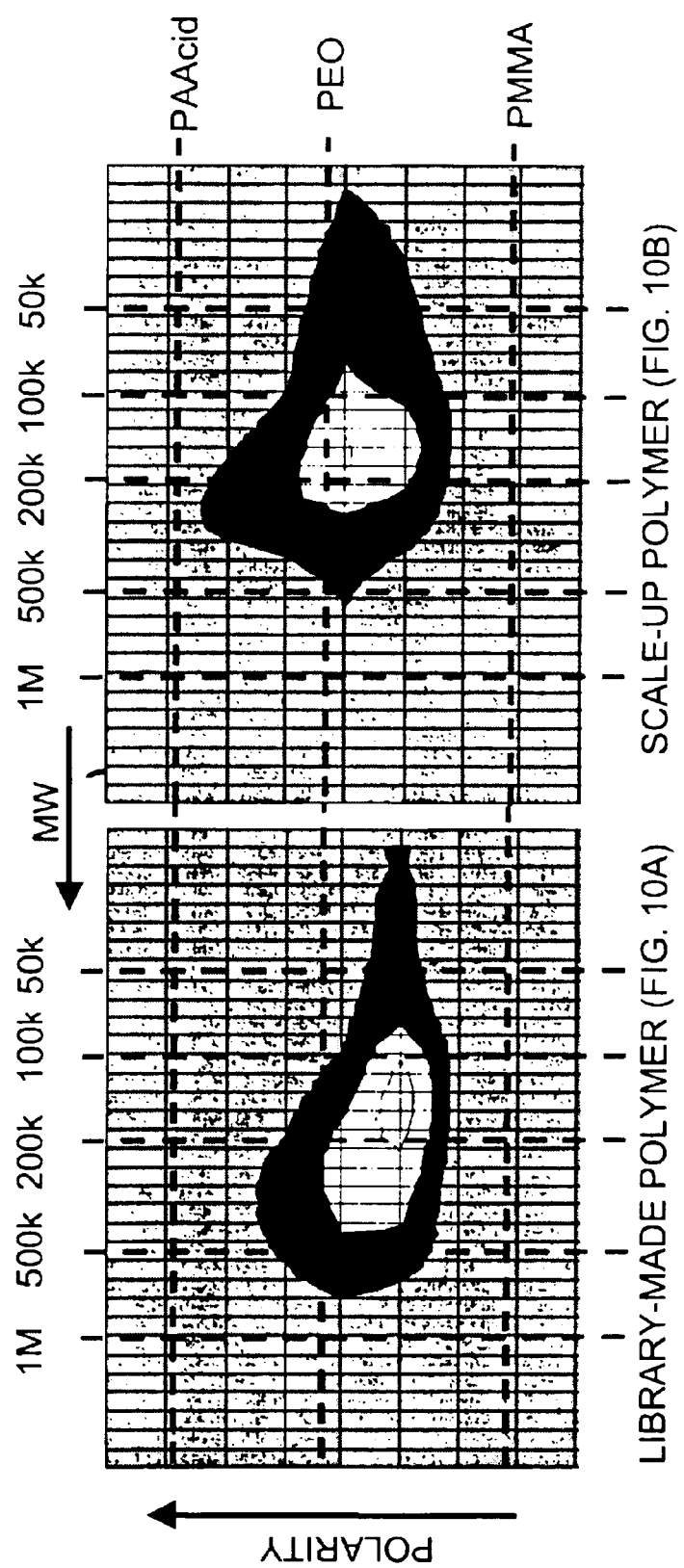
FIGS. 10A and 10B are 2-dimensional contour graphs showing chemical composition distribution, represented by polarity (as determined using normal-phase HPLC retention time in a first-dimension analysis), versus molecular weight distribution (as determined using GPC retention time in a second-dimension analysis) for a small-scale sample of interest (FIG. 10A) and for the corresponding scaled-up sample of interest (FIG. 10B).

Example 5
Use of 2-Dimensional Liquid Chromatography for Tuning of Polymerization Synthesis Conditions During Scale Up of Polymerization Process This example demonstrates two-dimensional liquid chromatography techniques for fingerprinting characterization as applied for tuning of polymerization synthesis conditions in an effort to scale up a polymerization process (e.g., from bench scale to pilot scale or from pilot scale to commercial production scale). The example also demonstrates two-dimensional liquid chromatography techniques as applied for polymerization process monitoring and/or polymerization process control In a first experiment, a library of polymer samples were synthesized and screened using combinatorial (high-throughput) techniques known in the art. One of the polymer samples was determined to have useful properties in the library-scale. The polymer sample of interest was a random copolymer. The polymer sample of interest of the library was characterized in a comprehensive, directly-coupled two-dimension liquid chromatography system comprising a first dimension HPLC subsystem adapted for normal-phase compositional gradient elution chromatography, and a second dimension HPLC subsystem adapted for gel permeation chromatography (GPC). The operational conditions and protocols for the two-dimensional liquid chromatography system was substantially the same as that described in connection with Example 1. The results are shown in FIG. 10, as a 2-dimensional contour graph showing chemical composition distribution, represented by polarity (as determined using normal-phase HPLC retention time in a first-dimension analysis), versus molecular weight distribution (as determined using GPC retention time in a second-dimension analysis).

During a scale up effort to prepare the same polymer sample of interest on a larger scale (scaling factor of about 1:1000), the two-dimensional chromatography analysis (under the same operational protocols and conditions) was used to tune the polymerization synthesis conditions for the scaled-up process, until the results of the two-dimensional analysis for the large-scale synthesis polymer sample, shown in FIG. 10B, was substantially the same as the results for the small scale synthesis polymer sample (FIG. 10A). As shown, FIG. 2B shows a 2-dimensional contour graph showing chemical composition distribution, represented by polarity (as determined using normal-phase HPLC retention time in a first-dimension analysis), versus molecular weight distribution (as determined using GPC retention time in a second-dimension analysis) for the large-scale synthesis polymer sample.

In light of the detailed description of the invention and the examples presented above, it can be appreciated that the several objects of the invention are achieved.

The explanations and illustrations presented herein are intended to acquaint others skilled in the art with the invention, its principles, and its practical application. Those skilled in the art may adapt and apply the invention in its numerous forms, as may be best suited to the requirements of a particular use. Accordingly, the specific embodiments of the present invention as set forth are not intended as being exhaustive or limiting of the invention.

What is claimed is:

1. A method for characterizing a polymer sample in a multi-dimensional liquid chromatography system, the method comprising:

injecting the polymer sample into a first-dimension mobile phase of a first dimension of the multi-dimensional liquid chromatography system;

chromatographically separating at least one sample component of the injected polymer sample from other sample components thereof in a first-dimension liquid chromatography column, such that a first-dimension mobile phase eluent from the first-dimension column comprises two or more first-dimension separated sample components;

sampling discrete volumes of the first-dimension mobile phase eluent at regularly recurring time intervals, such that at least a portion of each of the first-dimension separated sample components are sampled;

injecting each of the sampled volumes of the first-dimension mobile phase eluent directly into a second-dimension mobile phase of the second dimension of the multi-dimensional liquid chromatography system;

chromatographically separating at least one subcomponent of the sampled portions of each of the first-dimension separated sample components from other subcomponents thereof in a second-dimension liquid chromatography column, such that a second-dimension mobile phase eluent from the second-dimension column comprises two or more second-dimension separated subcomponents for each of the sampled portions of each of the first-dimension separated sample components; and detecting a property of the second-dimension separated subcomponents in the second-dimension mobile phase eluent using a flow-through detector.

2. The method of claim 1, further comprising controlling the sampling interval and sampling volume such that at least two discrete fractions of each of the first-dimension separated sample components are sampled.

3. The method of claim 1, further comprising controlling the sampling interval and sampling volume such that at least three discrete fractions of each of the first-dimension separated sample components are sampled.

4. The method of claim 1, wherein a discrete volume of the first-dimension mobile phase eluent is sampled at least once every two minutes.

5. The method of claim 1, wherein a discrete volume of the first-dimension mobile phase eluent is sampled at least once every 30 seconds.

6. The method of claim 1, wherein at least ten discrete volumes of the first-dimension mobile phase eluent are sampled.

7. The method of claim 1, wherein at least one hundred discrete volumes of the first-dimension mobile phase eluent are sampled.

8. The method of claim 1, wherein the sampled volumes of the first-dimension mobile phase eluent are not more than about 500 $\mu$l.

9. The method of claim 1, wherein the sampled volumes of the first-dimension mobile phase eluent are not more than about 250 $\mu$l.

10. The method of claim 1, wherein at least ten discrete volumes of the first-dimension mobile phase eluent are sampled with a sampling frequency of at least once every 30 seconds, and the sampled volumes are not more than about 250 $\mu$l.

11. The method of claim 1, wherein at least one of the sampled volumes of the first-dimension mobile phase eluent has an essential absence of first-dimension separated sample components.

12. The method of claim 1, further comprising determining a property of interest from the detected property of the second-dimension separated subcomponents.

13. The method of claim 1, further comprising detecting a property of the first-dimension separated components in the first-dimension mobile phase eluent using a flow-through detector.

14. The method of claim 1, wherein the property of the second-dimension separated subcomponents is detected using a concentration detector or mass detector.

15. The method of claim 1, wherein the property of the second-dimension separated subcomponents is detected using an evaporative light-scattering detector.

16. The method of claim 1, wherein at least one of the first dimension or second dimension of the multi-dimensional liquid chromatography system is a high-performance liquid chromatography subsystem adapted for size exclusion chromatography.

17. The method of claim 1, wherein at least one of the first dimension or second dimension of the multi-dimensional liquid chromatography system is a high-performance liquid chromatography subsystem adapted for gel permeation chromatography.

18. The method of claim 1, wherein the second dimension of the multi-dimensional liquid chromatography system is a high-performance liquid chromatography subsystem adapted for size exclusion chromatography.

19. The method of claim 1, wherein the second dimension of the multi-dimensional liquid chromatography system is a high-performance liquid chromatography subsystem adapted for gel permeation chromatography.

20. The method of claim 1, wherein the first dimension of the multi-dimensional liquid chromatography system is a high-performance liquid chromatography subsystem adapted for determining compositional variations of first-dimension separated sample components.

21. The method of claim 1, wherein the first dimension of the multi-dimensional liquid chromatography system is a high-performance liquid chromatography subsystem adapted for mobile-phase compositional gradient elution chromatography.

22. The method of claim 1, wherein the first dimension of the multi-dimensional liquid chromatography system is a high-performance liquid chromatography subsystem adapted for mobile-phase temperature gradient elution chromatography.

23. The method of claim 1, wherein the first dimension of the multi-dimensional liquid chromatography system is a high-performance liquid chromatography subsystem adapted for reverse phase chromatography.

24. The method of claim 1, wherein the first dimension of the multi-dimensional liquid chromatography system is a high-performance liquid chromatography subsystem adapted for adsorption chromatography.

25. The method of claim 1, wherein the first dimension of the multi-dimensional liquid chromatography system is a high-performance liquid chromatography subsystem adapted for determining compositional variations of first-dimension separated sample components, and the second dimension of the multi-dimensional liquid chromatography system is a high-performance liquid chromatography subsystem adapted for size exclusion chromatography.

26. The method of claim 1, wherein the polymer sample is a non-biological polymer sample.

27. The method of claim 1, wherein the polymer sample is a biological polymer sample.

28. The method of claim 1, wherein the polymer sample being characterized is a member of a library of polymer samples comprising four or more different polymer samples, the method further comprising:
repeating the steps of injecting a polymer sample into the first-dimension mobile phase, separating a component of the polymer sample in the first-dimension liquid chromatography column, sampling the first-dimension mobile phase eluent, injecting sampled volumes in to the second-dimension mobile phase, separating a subcomponent of sampled portions of the first-dimension separated components in the second-dimension liquid chromatography column, and detecting a property of the second-dimension separated subcomponents for each of the polymer samples of the library.

29. The method of claim 1, wherein the polymer sample is a polymerization product mixture that is untreated or pretreated only with one or more steps selected from the group consisting of non-chromatographic separation, dilution, mixing, and redissolution.

30. A method for characterizing a polymer sample in a multi-dimensional liquid chromatography system, the method comprising:
injecting the polymer sample into a first-dimension mobile phase of a first dimension of the multi-dimensional liquid chromatography system, wherein the first dimension of the multi-dimensional liquid chromatography system is a high-performance liquid chromatography subsystem adapted for determining compositional variations of first-dimension separated sample components;
chromatographically separating at least one sample component of the injected polymer sample from other sample components thereof in a first-dimension liquid chromatography column, such that a first-dimension mobile phase eluent from the first-dimension column comprises two or more first-dimension separated sample components;
sampling discrete volumes of the first-dimension mobile phase eluent at regularly recurring time intervals, such that at least a portion of each of the first-dimension separated sample components are sampled;
injecting each of the sampled volumes of the first-dimension mobile phase eluent directly into a second-dimension mobile phase of the second dimension of the multi-dimensional liquid chromatography system, wherein the second dimension of the multi-dimensional liquid chromatography system is a high-performance liquid chromatography subsystem adapted for size exclusion chromatography;
chromatographically separating at least one subcomponent of the sampled portions of each of the first-dimension separated sample components from other subcomponents thereof in a second-dimension liquid chromatography column, such that a second-dimension mobile phase eluent from the second-dimension column comprises two or more second-dimension separated subcomponents for each of the sampled portions of each of the first-dimension separated sample components; and
detecting a property of the second-dimension separated subcomponents in the second-dimension mobile phase eluent using a flow-through detector.

31. The method of claim 30, wherein the first dimension of the multi-dimensional liquid chromatography system is a high-performance liquid chromatography subsystem adapted for mobile-phase compositional gradient elution chromatography.

32. The method of claim 30, wherein the first dimension of the multi-dimensional liquid chromatography system is a high-performance liquid chromatography subsystem adapted for mobile-phase temperature gradient elution chromatography.

33. The method of claim 30, wherein the first dimension of the multi-dimensional liquid chromatography system is a high-performance liquid chromatography subsystem adapted for reverse phase chromatography.

34. The method of claim 30, wherein the first dimension of the multi-dimensional liquid chromatography system is a high-performance liquid chromatography subsystem adapted for adsorption chromatography.

35. A method for characterizing a polymer sample in a multi-dimensional liquid chromatography system, the method comprising:
injecting the polymer sample into a first-dimension mobile phase of a first dimension of the multi-dimensional liquid chromatography system, wherein the polymer sample is a member of a library of polymer samples comprising four or more different polymer samples;
chromatographically separating at least one sample component of the injected polymer sample from other sample components thereof in a first-dimension liquid chromatography column, such that a first-dimension mobile phase eluent from the first-dimension column comprises two or more first-dimension separated sample components;
sampling discrete volumes of the first-dimension mobile phase eluent at regularly recurring time intervals, such that at least a portion of each of the first-dimension separated sample components are sampled;
injecting each of the sampled volumes of the first-dimension mobile phase eluent directly into a second-dimension mobile phase of the second dimension of the multi-dimensional liquid chromatography system;
chromatographically separating at least one subcomponent of the sampled portions of each of the first-dimension separated sample components from other subcomponents thereof in a second-dimension liquid chromatography column, such that a second-dimension mobile phase eluent from the second-dimension column comprises two or more second-dimension separated subcomponents for each of the sampled portions of each of the first-dimension separated sample components;
detecting a property of the second-dimension separated subcomponents in the second-dimension mobile phase eluent using a flow-through detector; and
repeating the steps of injecting a polymer sample into the first-dimension mobile phase, separating a component of the polymer sample in the first-dimension liquid chromatography column, sampling the first-dimension mobile phase eluent, injecting sampled volumes in to the second-dimension mobile phase, separating a subcomponent of sampled portions of the first-dimension separated components in the second-dimension liquid chromatography column, and detecting a property of the second-dimension separated subcomponents for each of the polymer samples of the library.

36. The method of claim 35, wherein the polymer samples of the library are non-biological polymer samples.

37. The method of claim 35, wherein the library comprises four or more different non-biological polymers on a common substrate.

38. The method of claim 35, wherein the library comprises four or more different non-biological polymers synthesized in a parallel reaction vessel.

39. The method of claim 35, wherein the four or more different non-biological polymer samples are polymerization product mixtures resulting from parallel polymerization reactions that are varied with respect to a factor affecting polymerization.

40. The method of claim 35, wherein the four or more different non-biological polymer samples are polymerization product mixtures resulting from parallel polymerization reactions that are varied with respect to one or more of reactant materials, catalysts, catalysts precursors, initiators, additives, or the relative amounts thereof.

41. The method of claim 35, wherein the four or more different non-biological polymer samples are polymerization product mixtures resulting from parallel polymerization reactions that are varied with respect to reaction conditions.

* * * * *

UNITED STATES PATENT AND TRADEMARK OFFICE
CERTIFICATE OF CORRECTION

PATENT NO. : 6,730,228 B2
DATED : May 4, 2004
INVENTOR(S) : Petro et al.

It is certified that error appears in the above-identified patent and that said Letters Patent is hereby corrected as shown below:

<u>Title page,</u>
Item [56], References Cited, U.S. PATENT DOCUMENTS, include entry of reference -- U.S. Patent Publication No. 2002/0098471 --.

Signed and Sealed this

Twenty-eighth Day of June, 2005

JON W. DUDAS
*Director of the United States Patent and Trademark Office*